(12) United States Patent
Singh et al.

(10) Patent No.: US 12,203,950 B2
(45) Date of Patent: Jan. 21, 2025

(54) QUALITY CONTROL SUPPORT METHOD, QUALITY CONTROL SUPPORT SYSTEM, QUALITY CONTROL SUPPORT DEVICE, AND PROGRAM

(71) Applicant: SYSMEX CORPORATION, Kobe (JP)

(72) Inventors: Shrey Singh, Kobe (JP); Takashi Karino, Kobe (JP); David Peschard, Le Plessis Robinson (FR); Mattheus Johannes Hofman, Meeden (NL); James Donald Hart, Hamburg (DE)

(73) Assignee: SYSMEX CORPORATION, Kobe (JP)

( * ) Notice: Subject to any disclaimer, the term of this patent is extended or adjusted under 35 U.S.C. 154(b) by 315 days.

(21) Appl. No.: 17/382,785

(22) Filed: Jul. 22, 2021

(65) Prior Publication Data
US 2022/0034922 A1 Feb. 3, 2022

(30) Foreign Application Priority Data

Jul. 31, 2020 (JP) ................................ 2020-130438

(51) Int. Cl.
*G01N 35/00* (2006.01)
(52) U.S. Cl.
CPC . *G01N 35/00623* (2013.01); *G01N 35/00693* (2013.01); *G01N 35/00712* (2013.01);
(Continued)

(58) Field of Classification Search
CPC ............ G06F 3/0484; G01N 35/00623; G01N 35/00693; G01N 35/00712;
(Continued)

(56) References Cited

U.S. PATENT DOCUMENTS 9,483,441 B2 * 11/2016 Li ........................... G06F 17/00
2014/0068489 A1 3/2014 Wyland et al.

FOREIGN PATENT DOCUMENTS

EP 3546950 A1 10/2019
EP 3578993 A1 12/2019
(Continued)

OTHER PUBLICATIONS

Extended European search report issued on Jan. 5, 2022 in European patent application No. 21187161.1.
(Continued)

*Primary Examiner* — Shogo Sasaki
(74) *Attorney, Agent, or Firm* — Crowell & Moring LLP

(57) ABSTRACT

A quality control support method for displaying a control chart of quality control related to an analyzer that measures a subject sample, the method comprising: generating a first control chart showing results of measured quality control substances by the analyzer in a first period; receiving a designation of a second period different from the first period, the second period being shorter than the first period and at least partially overlapping with the first period; generating a second control chart showing results of the measured subject samples by the analyzer in the second period; displaying the generated first control chart; and displaying the generated second control, is provided.

23 Claims, 32 Drawing Sheets

(52) U.S. Cl.
CPC ............... *G01N 35/00871* (2013.01); *G01N 2035/00811* (2013.01); *G01N 2035/00881* (2013.01); *G01N 2035/0091* (2013.01)

(58) Field of Classification Search
CPC ....... G01N 35/00613; G01N 35/00871; G01N 2035/00881; G01N 2035/0091; G01N 2035/00811; G16H 40/40
See application file for complete search history.

(56) References Cited

FOREIGN PATENT DOCUMENTS

| JP | 2009-180616 A | 8/2009 |
|---|---|---|
| JP | 2012-233799 A | 11/2012 |
| JP | 2015-194903 A | 11/2015 |
| JP | 2019-174424 A | 10/2019 |
| WO | 2018/142871 A1 | 8/2018 |

OTHER PUBLICATIONS

Tze Ping Loh et al., "Recommendations for laboratory informatics specifications needed for the application of patient-based real time quality control", Clinica Chimica Acta, 2019, pp. 625-629, vol. 495, Elsevier.
A copy of the extended European search report issued on Oct. 10, 2023 in a counterpart European patent application No. 23179194.8, 11 pages.
The Japanese Office Action issued on Mar. 28, 2024 in a counterpart Japanese patent application No. 2020-130438, 10 pages.
The Japanese Office Action issued on Aug. 27, 2024 in a counterpart Japanese patent application No. 2020-130438 (6 pages).

* cited by examiner

QC sample measurement data collection

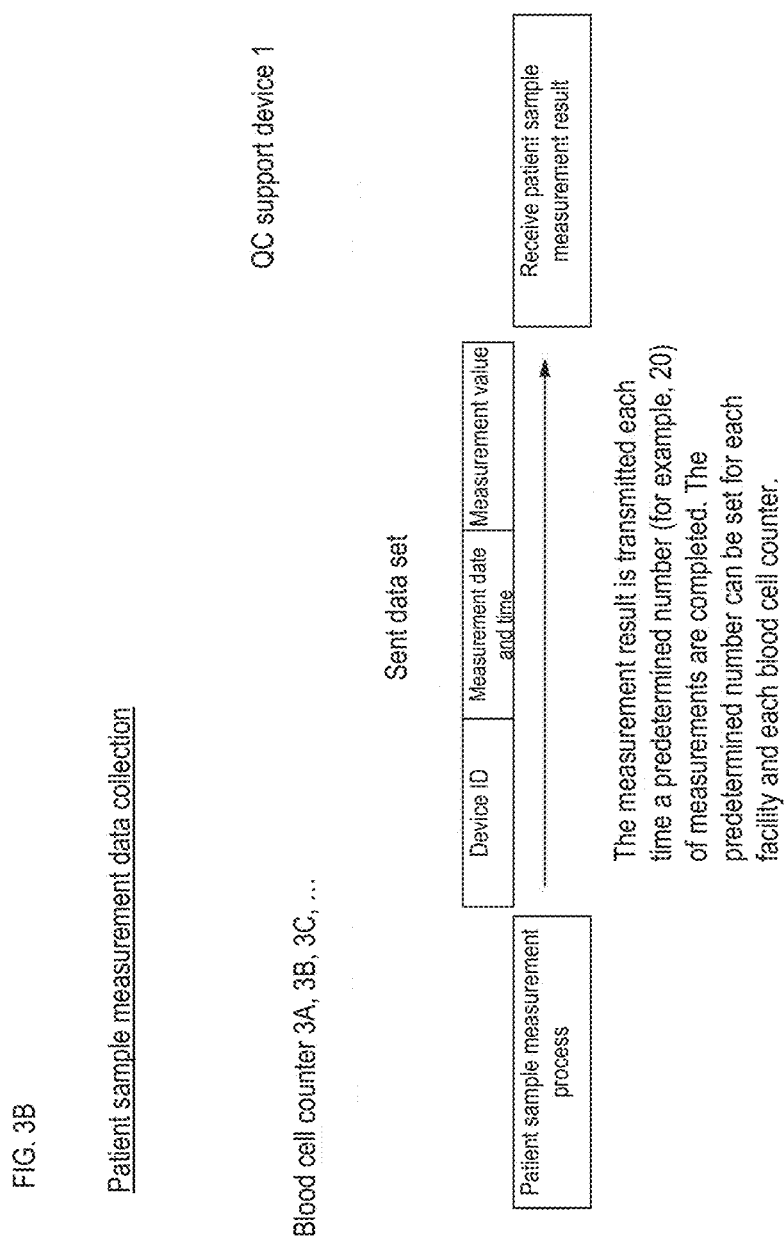

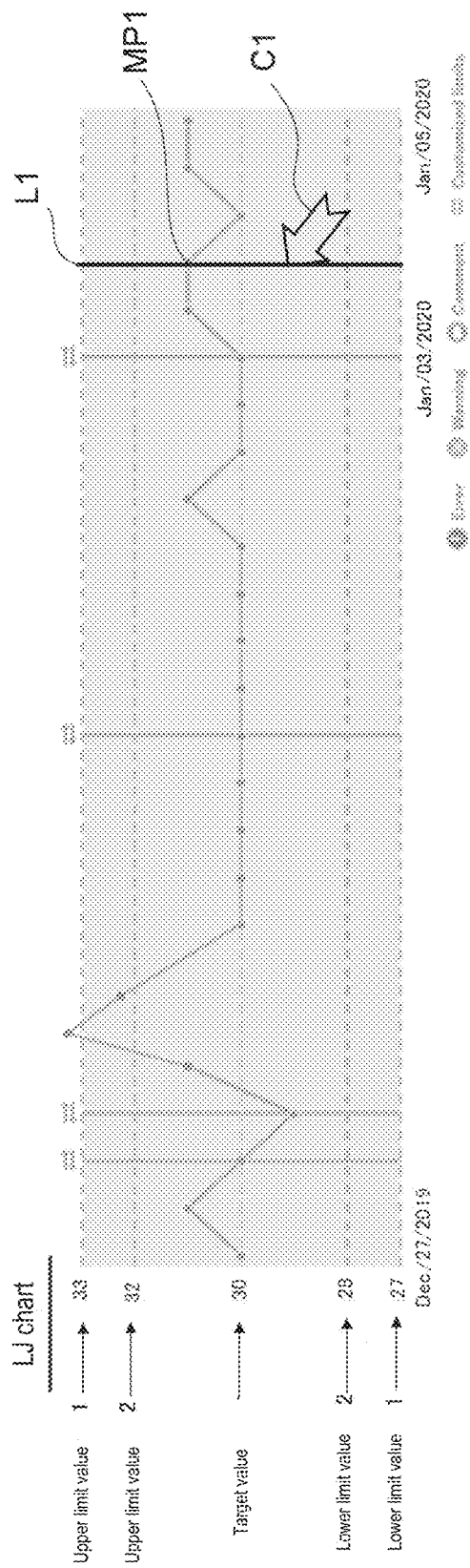

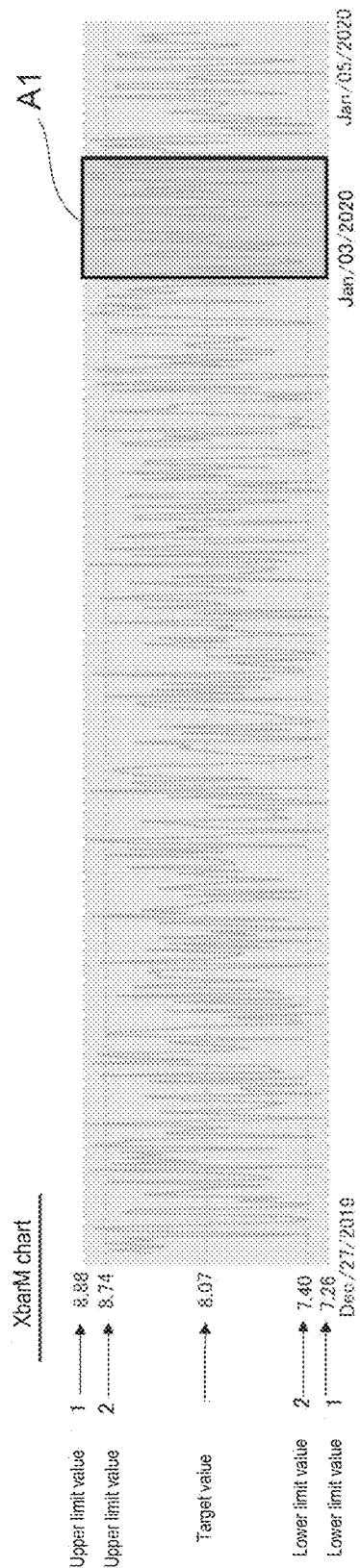

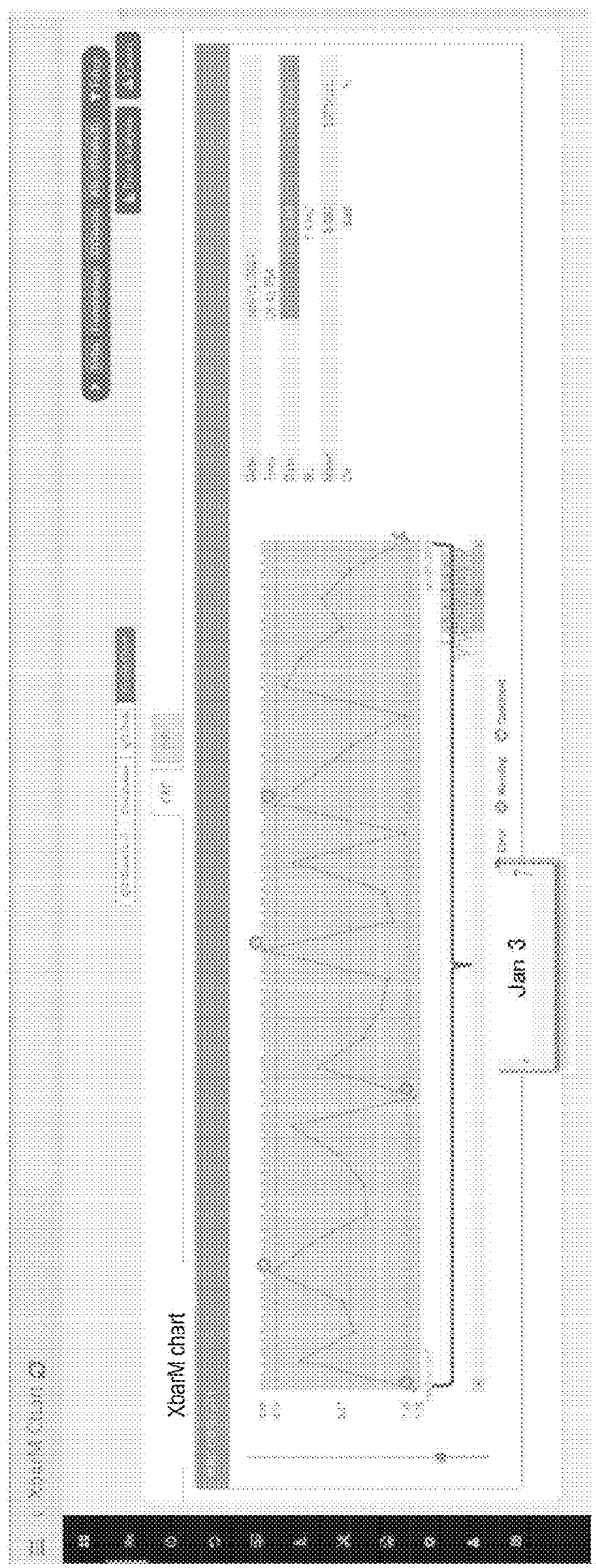

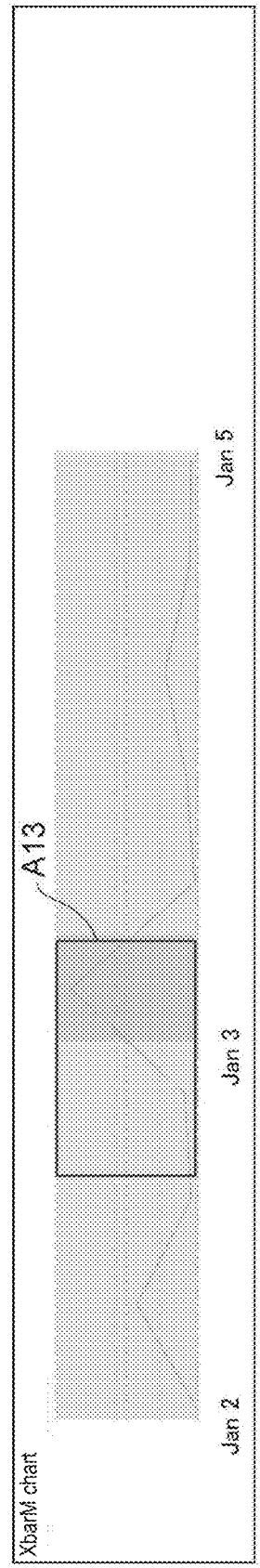

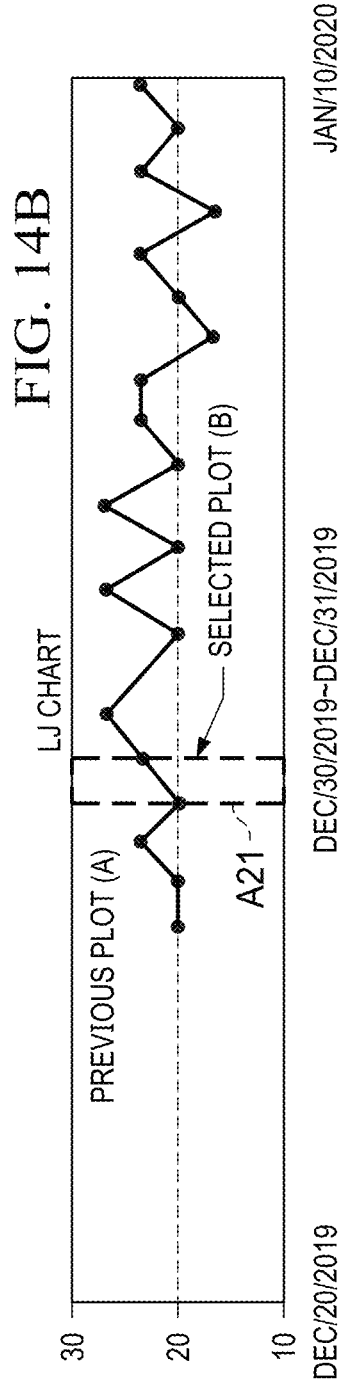

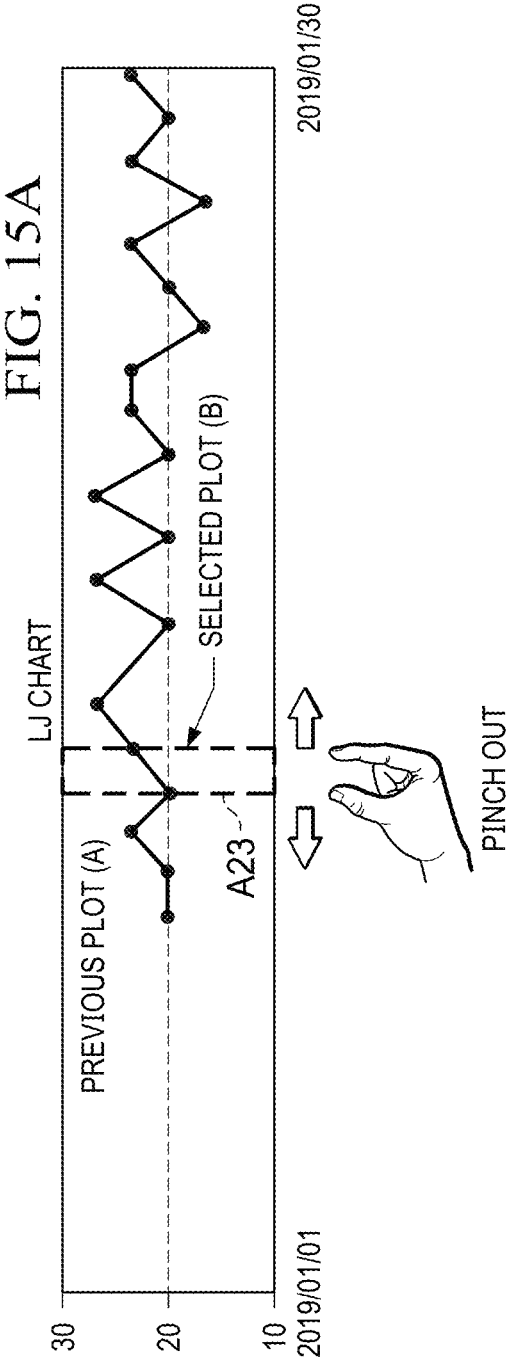

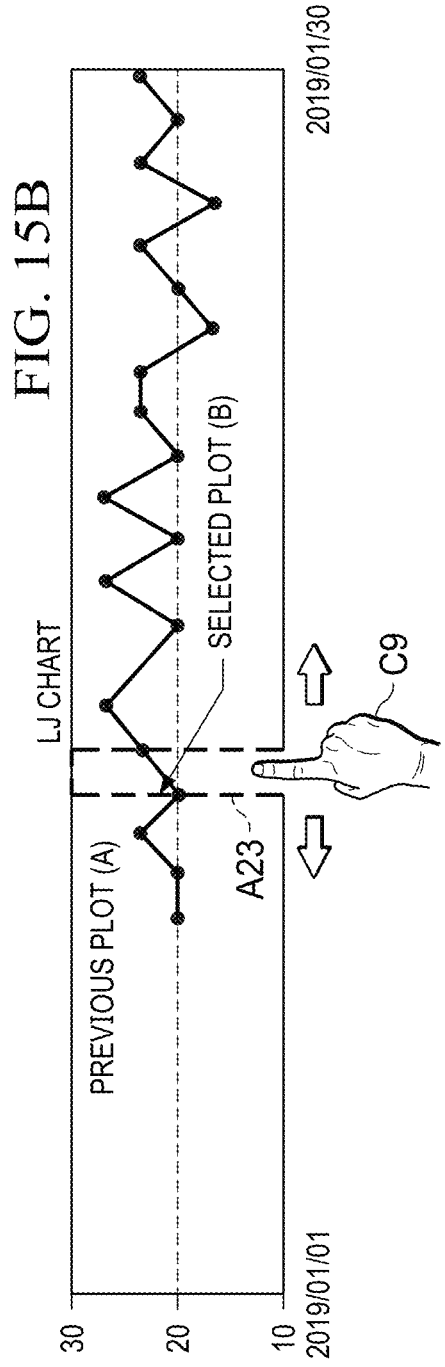

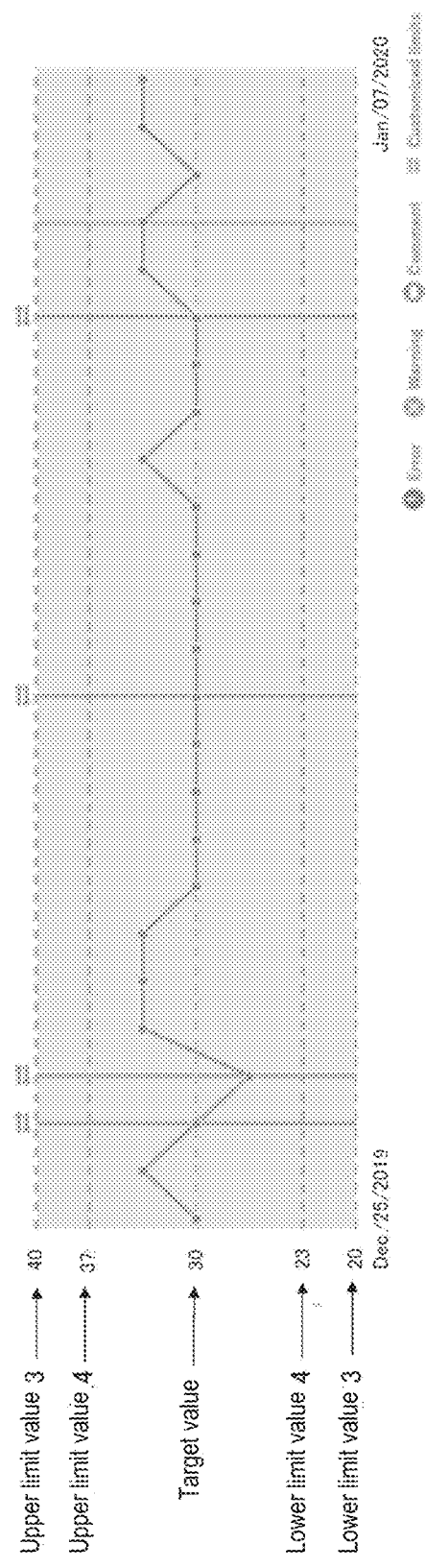

QUALITY CONTROL SUPPORT METHOD, QUALITY CONTROL SUPPORT SYSTEM, QUALITY CONTROL SUPPORT DEVICE, AND PROGRAM

RELATED APPLICATIONS

This application claims priority to Japanese Patent Application No. 2020-130438, filed on Jul. 31, 2020, the entire content of which is incorporated herein by reference.

BACKGROUND OF THE INVENTION

1. Field of the Invention

The present invention relates to a quality control support method, a quality control support system, a quality control support device, and a program.

2. Description of the Related Art

A method using a control chart by the LJ (Levey-Jennings) method, measurement results of quality control substances prepared to obtain predetermined measured values in chronological order, and a method using a control chart showing the average value transition of the measurement results of a subject sample without using a quality control substance are known as quality control methods. When there is an abnormality in the measurement result, it is possible to identify whether the cause is the analyzer, the reagent used in the analyzer, or the quality control substance by checking these control charts. Also described is an example displaying a control chart (control chart showing the result of PBRTQC (Patient-Based Real Time Quality Control)) showing the average value transition of the measurement result of the subject sample as a method of supporting quality control.

The number of measurements of quality control substances (plot of control chart by LJ method) is generally 1 to 3 times a day, whereas the number of measurements of subject samples may be tens to hundreds of times. Since the control chart by the LJ method and the control chart showing the result of PBRTQC are displayed in the same period in the method described in Lo TP, Cervinski M A, et al., "Recommendations for laboratory informatics specifications needed for the application of patient-based real time quality control", Clinica Chimica Acta, 2019 August, 495, pages 625-629, if the display period is shortened, for example, it is difficult to grasp the transition the measurement result of the quality control substances over a long period of time, such as 2 weeks, and if the display time is lengthened for example, it is difficult to grasp the transition of the measurement result of the subject sample in a short period such as one day. Therefore, even if the method described in Lo TP, Cervinski M A, et al., "Recommendations for laboratory informatics specifications needed for the application of patient-based real time quality control", Clinica Chimica Acta, 2019 August, 495, pages 625-629 is used, it is difficult to identify the cause when there is an abnormality in the measurement result.

SUMMARY OF THE INVENTION

The present invention provides a quality control support method, a quality control support system, a quality control support device, and a program that facilitates identification of the cause when an abnormality is found in a measurement result.

The quality control support method according to an aspect of the present invention is a quality control support method for displaying a control chart of quality control related to an analyzer that measures a subject sample, the method comprising: generating a first control chart showing results of measured quality control substances by the analyzer in a first period; receiving a designation of a second period different from the first period, the second period being shorter than the first period and at least partially overlapping with the first period; generating a second control chart showing results of the measured subject samples by the analyzer in the second period; displaying the generated first control chart; and displaying the generated second control chart.

According to the above aspect, the above-mentioned quality control support method displays the first control chart in the first period, receives the designation of the second period, which is different from the first period, shorter than the first period, and at least partially overlaps with the first period, and displays the second control chart in the second period. Therefore, in the above quality control support method, the first control chart and the second control chart are displayed in the display period according to the difference between the measurement frequency of the quality control substance and the measurement frequency of the subject sample. Accordingly, the cause can be easily identified when there is an abnormality in the measurement result. Receiving the designation of the second period separately from the designation of the first period is to receive the designation of the designation of the second period separately from the first period preset as the default period, or an arbitrarily designated first period. When an arbitrary first period is designated, the timing of receiving the designation may be different from each other or simultaneous with each other in the first period and the second period.

The quality control support method according to one aspect of the present invention is a quality control support method for displaying a control chart of quality control related to an analyzer that measures a subject sample, the method comprising: generating a first control chart showing results of measured quality control substances by the analyzer in a first period; generating a second control chart showing results of measured subject samples by the analyzer in a second period, which is a part of the first period; and displaying the first control chart and the second control chart side by side.

According to the above aspect, the quality control support method displays the first control chart in the first period, and displays the second control chart in the second period, which is a part of the first period, and displays the first control chart and the second control chart side by side. Therefore, in the above quality control support method, the first control chart and the second control chart are displayed side by side in the display period according to the difference between the measurement frequency of the quality control substance and the measurement frequency of the subject sample. Accordingly, since the first control chart and the second control chart are displayed side by side, the cause can be more easily identified when there is an abnormality in the measurement result.

The quality control support system according to one aspect of the present invention is a quality control support system for displaying a control chart of quality control related to an analyzer that measures a subject sample, the system comprising: a quality control support device comprising a first control unit; a terminal device, which is connected to the quality control support device via a network, comprising a second control unit and a display;

wherein the first control unit of the quality control support device is configured to execute operations comprising: generating a first control chart showing results of measured quality control substances by the analyzer in a first period; receiving a designation of a second period different from the first period, the second period being shorter than the first period and at least partially overlapping with the first period; generating a second control chart showing results of measured subject samples by the analyzer in the second period; and the second control unit of the terminal device is configured to execute: displaying the generated first control chart on the display; and displaying the generated second control chart on the display.

According to the above aspect, the quality control support system displays the first control chart in the first period, receives the designation of the second period, which is shorter than the first period and at least partially overlaps with the first period, separately from the designation of the first period, and displays the second control chart in the second period. Therefore, in the above quality control support method, the first control chart and the second control chart are displayed in the display period according to the difference between the measurement frequency of the quality control substance and the measurement frequency of the subject sample. Accordingly, the cause can be easily identified when there is an abnormality in the measurement result.

The quality control support device according to one aspect of the present invention is a quality control support device for displaying a control chart of quality control related to an analyzer that measures a subject sample, the device comprising: a control unit; and a display; wherein the control unit is configured to execute operations comprising: generating a first control chart showing results of measured quality control substances by the analyzer in a first period; receiving a designation of a second period different from the first period, the second period being shorter than the first period and at least partially overlapping with the first period; generating a second control chart showing results of the measured subject samples by the analyzer in the second period; displaying the generated first control chart on the display; and displaying the generated second control chart on the display.

According to the above aspect, the quality control support device displays the first control chart in the first period, receives the designation of the second period, which is shorter than the first period and at least partially overlaps with the first period, separately from the designation of the first period, and displays the second control chart in the second period. Therefore, in the above quality control support device, the first control chart and the second control chart are displayed in the display period according to the difference between the measurement frequency of the quality control substance and the measurement frequency of the subject sample. Accordingly, the cause can be easily identified when there is an abnormality in the measurement result.

The quality control support device according to one aspect of the present invention is a quality control support device that is connected to a terminal device comprising a display via a network and displays a control chart of quality control related to an analyzer that measures a subject sample on a display of the terminal device, the quality control support devise comprising: a control unit, wherein the control unit is configured to execute operations comprising: generating a first control chart showing results of measured quality control substances by the analyzer in a first period; receiving a designation of a second period different from the first period, the second period being shorter than the first period and at least partially overlapping with the first period; generating a second control chart showing results of the measured subject samples by the analyzer in the second period; sending the generated first control chart to the terminal device; and sending the generated second control chart to the terminal device.

According to the above aspect, the quality control support device generates the first control chart in the first period, receives the designation of the second period, which is shorter than the first period and at least partially overlaps with the first period, separately from the designation of the first period, and generates a second control chart in the second period. The quality control support device transmits the generated first control chart to the terminal device, and transmits the generated second control chart to the terminal device. Therefore, in the terminal device connected to the quality control support device via the network and equipped with a display, the first control chart and the second control chart are displayed in a display period according to the difference between the measurement frequency of the quality control substance and the measurement frequency of the subject sample. Accordingly, the cause can be easily identified when there is an abnormality in the measurement result.

The program according to one aspect of the invention is a program in a quality control support device that displays a control chart of quality control related to an analyzer that measures a subject sample on a display of a terminal device, the quality control support device and the terminal device being connected via the network, the program executing operations comprising: generating a first control chart showing results of measured quality control substances by the analyzer in a first period; receiving a designation of a second period different from the first period, the second period being shorter than the first period and at least partially overlapping with the first period; generating a second control chart showing results of the measured subject samples by the analyzer in the second period; sending the generated first control chart to the terminal device; and sending the generated second control chart to the terminal device.

According to the above aspect, the program, in the quality control support device, executes operations for generating the first control chart in the first period, receiving the designation of the second period, which is shorter than the first period and at least partially overlaps with the first period, separately from the designation of the first period, and generating a second control chart in the second period. In the quality control support device, the program executes operations for sending the generated first control chart to the terminal device, and sending the generated second control chart to the terminal device. Therefore, in the terminal device connected to the quality control support device via the network and equipped with a display, the first control chart and the second control chart are displayed in a display period according to the difference between the measurement frequency of the quality control substance and the measurement frequency of the subject sample. Accordingly, the cause can be easily identified when there is an abnormality in the measurement result.

The program of one aspect of the invention is a program in a quality control support device comprising a display that displays a control chart of quality control related to an analyzer that measures a subject sample, the program executing operations comprising: generating a first control chart showing results of measured quality control substances by the analyzer in a first period; receiving a designation of a second period different from the first period, the second period being shorter than the first period and at least partially overlapping with the first period; generating a second control chart showing results of the measured subject samples by the analyzer in the second period; displaying the generated first control chart on the display; and displaying the generated second control chart on the display.

According to the above aspect, the program, in the quality control support device, executes operations for generating the first control chart in the first period, receiving the designation of a second period, which is different from the first period, shorter than the first period and at least partially overlaps with the first period, generating a second control chart in the second period, displaying the generated first control chart on the display, and displaying the generated second control chart on the display. Therefore, in the above quality control support device, the program displays the first control chart and the second control chart in the display period according to the difference between the measurement frequency of the quality control substance and the measurement frequency of the subject sample. Accordingly, the cause can be easily identified when there is an abnormality in the measurement result.

According to the present invention, it is possible to provide a quality control support technique that facilitates identification of the cause when an abnormality is found in the measurement result.

BRIEF DESCRIPTION OF THE DRAWINGS

FIG. 3B is a diagram showing an example of a measurement data collection process of a subject sample measurement process in a blood cell counter;

FIG. 5A is a diagram showing an example of an LJ chart;

FIG. 5B is a diagram showing an example of an XbarM chart;

FIG. 6B is a diagram showing an example of an XbarM chart;

FIG. 8B is a diagram showing an example of an XbarM chart displayed when a predetermined operation is executed in the XbarM chart of FIG. 8A;

FIG. 14B is a diagram showing an example of an LJ chart showing a period corresponding to a period specified on the display period designation screen of the XbarM chart shown in FIG. 14A;

FIG. 15A is an example showing an example of size control of a specific region in an LJ chart;

FIG. 15B is an example showing an example of position control of a specific region in the LJ chart;

FIG. 20 is a diagram showing an example of an LJ chart according to a second embodiment;

DETAILED DESCRIPTION OF THE PREFERRED EMBODIMENTS

Figure 1:
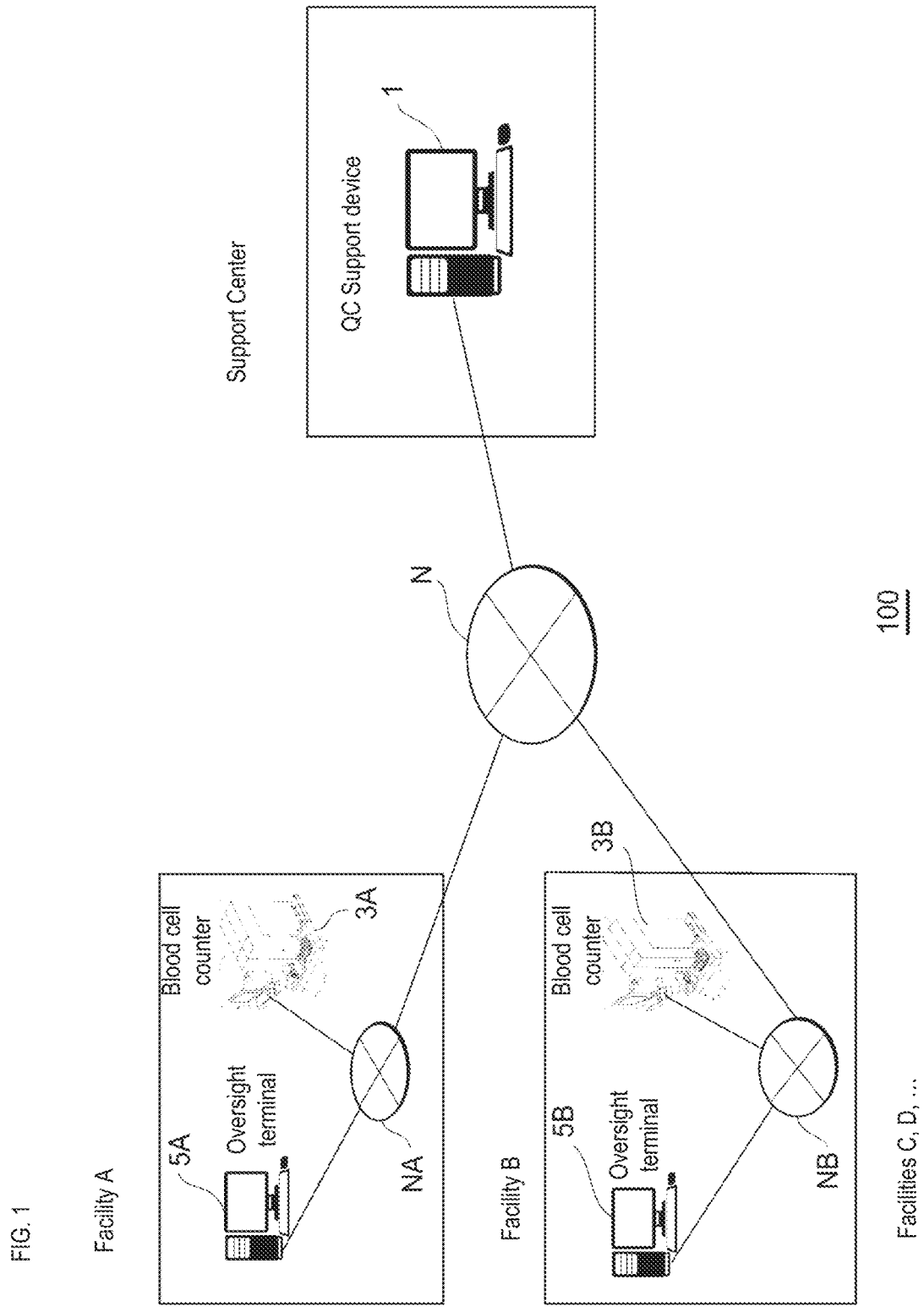
FIG. 1 is a diagram showing an example of a structure of a quality control support system according to a first embodiment.

Hereinafter, preferred embodiments of the present invention will be described with reference to the drawings. Note that the same elements are designated by the same reference numerals, and duplicate description will be omitted. The positional relationship such as up, down, left, and right shall be based on the positional relationship shown in the drawings unless otherwise specified. The dimensional ratios in the drawings are not limited to the ratios shown. The following embodiments are examples for explaining the present invention, and the present invention is not limited to these embodiments.

First Embodiment

FIG. 1 is a diagram showing an example of the structure of the quality control support system according to the first embodiment. As shown in FIG. 1, the quality control support system 100 illustratively includes a quality control support device 1, a blood cell counter 3A and an oversight terminal 5A arranged in facility A, and a blood cell counter 3B and an oversight terminal 5B arranged in facility B. The quality control support device 1 is a device that displays various charts (control charts) of quality control related to the blood cell counter 3 that measures a subject sample, and/or generates display information for display on another computer.

The blood cell counter 3 is a device for measuring a subject sample. The blood cell counter 3 performs measurement (QC measurement) on the quality control substance, for example, once or twice a day. The blood cell counter 3 performs measurements on subject samples, for example, tens to hundreds of times a day. The oversight terminal 5 is, for example, a device operated by a person working at the facility, and executes various processes related to the management of the entire facility. The oversight terminal 5 receives from the person in charge an instruction to display various charts of quality control related to the blood cell counter 3 or an input regarding a display period. The oversight terminal 5 inputs the input.

Upon receipt, the corresponding control signal is transmitted to the quality control support device 1. When the oversight terminal 5 receives the information for displaying the various charts generated by the quality control support device 1, the oversight terminal 5 displays various charts on the display provided in the oversight terminal 5 based on the received information.

By providing the quality control support system 100 with the quality control support device 1 and the oversight terminal 5A, the processing can be distributed to the quality control support device 1 and the oversight terminal 5A. Therefore, it is possible to prevent the oversight terminal 5A from slowing down processing other than displaying various charts, such as viewing inspection results and creating inspection reports.

Each of the facilities A and B includes, for example, a clinical laboratory, a clinical laboratory center, or the like. When facilities A and B are not distinguished, they are referred to as "facility" below. The number of facilities may be two or less, or three or more. In the first embodiment, each facility is managed by a different management entity. As described in the second embodiment described later, two or more facilities among the plurality of facilities may be managed by the same management entity. When the blood cell counter 3A and the blood cell counter 3B are not distinguished, they are referred to as "blood cell counter 3" (analyzer). Further, when the oversight terminal 5A and the oversight terminal 5B are not distinguished, it is referred to as "oversight terminal 5". Note that the number of blood cell counter 3 and the oversight terminal 5 arranged in each facility may be two or more.

Each facility and the support center (accuracy control support device 1) are communicably connected via the communication network N. At the facility A, the blood cell counter 3A and the oversight terminal 5A are connected to each other so as to be able to communicate with each other via the communication network NA. At the facility B, the blood cell counter 3B and the oversight terminal 5B are communicably connected to each other via the communication network NB. Each communication network comprises a wired and/or wireless network.

Figure 2:
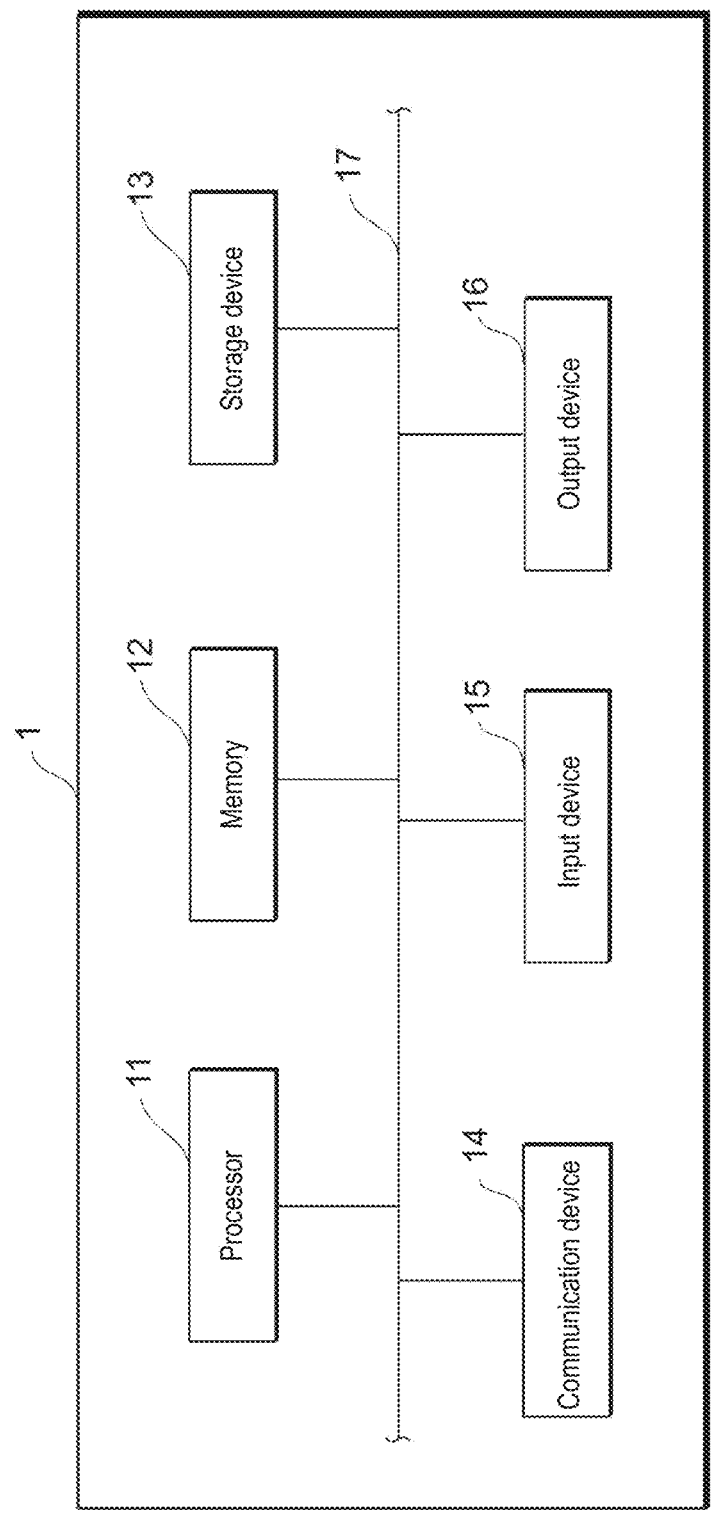
FIG. 2 is a diagram showing an example of a structure of a quality control support device and an oversight terminal according to the first embodiment.

FIG. 2 is a diagram showing an example of the hardware structure of the quality control support device 1 and the oversight terminal 5 according to the first embodiment. As shown in FIG. 2, the quality control support device 1 includes, for example, a processor 11 (control unit), a memory 12, a storage device 13, a communication device 14, an input device 15, and an output device 16.

The processor 11 is configured to control the operation of each part of the quality control support device 1. The processor 11 includes, for example, a CPU (Central Processing Unit), a DSP (Digital Signal Processor), an ASIC (Application Specific Integrated Circuit), a PLD (Programmable Logic Device), an FPGA (Field Programmable Gate Array), and a SoC (System-on-a-chip) and other integrated circuits. Each function such as the display processing function in the processor 11 is executed by executing the program stored in the memory 12 or the storage device 13.

The memory 12 is mainly used as a temporary storage area for performing data processing. The storage device 13 is mainly configured to store a program, a large amount of data, and the like. The memory 12 is composed of, for example, a ROM (Read Only Memory), an EPROM (Erasable Programmable ROM), an EEPROM (Electrically Erasable Programmable ROM), and/or a RAM (Random Access Memory). The storage device 13 is composed of, for example, a storage such as an HDD (Hard Disk Drive), an SSD (Solid State Drive) and/or an eMMC (embedded Multi Media Card).

The communication device 14 is configured to communicate with the blood cell counter 3 and the oversight terminal 5 at each facility via the communication network N shown in FIG. 1. The communication device 14 includes, for example, a network card, a communication module, and the like. The communication device 14 also may include an amplifier, an RF (Radio Frequency) device that performs processing related to radio signals, and the like.

The input device 15 is configured so that information can be input by a user operation in the support center. The input device 15 includes, for example, a keyboard, a pointing device, and/or a microphone. Examples of pointing devices include a mouse, a trackball, a touchpad, and a touch panel.

The output device 16 is configured to output information. The output device 16 includes, for example, a liquid crystal display, an EL (Electroluminescence) display, a display device such as a plasma display, and/or a speaker. The output device 16 also may further include the function of the input device 15. For example, the output device 16 also may be a device including a touch panel display.

The oversight terminal 5A includes a processor 11 (control unit), a memory 12, a storage device 13, a communication device 14, an input device 15, and an output device 16 as in the quality control support device 1.

Figure 3A:
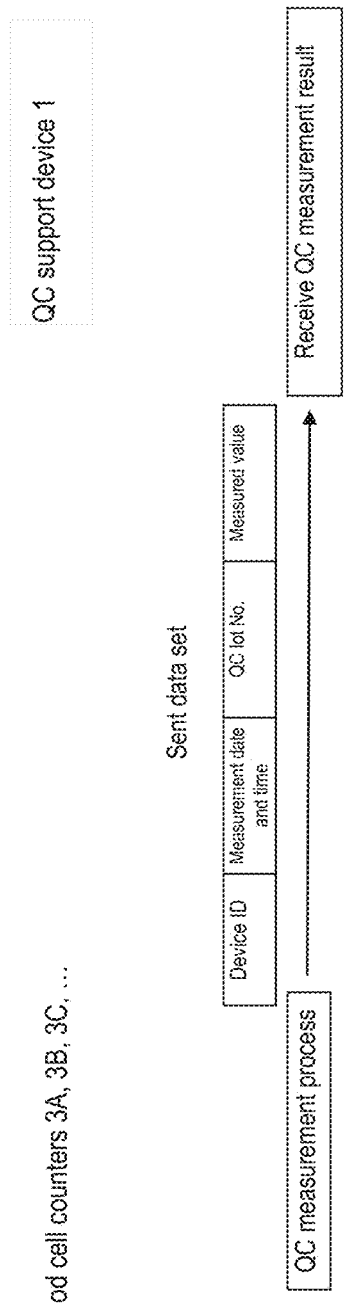
FIG. 3A is a diagram showing an example of a measurement data collection process of a QC (Quality Control) measurement process in a blood cell counter.

FIG. 3 is a diagram showing an outline of an outline of a measurement data collection process of the blood cell counter according to the embodiment. FIG. 3A is a diagram showing an example of a measurement data collection process of the QC measurement process (quality control measurement process) in the blood cell counter 3. FIG. 3B is a diagram showing an example of a measurement data collection process of the measurement process of the patient sample (subject sample) in the blood cell counter 3.

As shown in FIG. 3A, each of the blood cell counters 3 transmits a predetermined data set including the result of the measurement process relating to the quality control substance to the quality control support device 1. The transmitted data set includes the device ID of the blood cell counter 3, the measurement date and time, the lot number of the quality control substance, and the measured value in association with each other. When the measurement is completed, the measurement result regarding the quality control substance is transmitted to the quality control support device 1. The measurement result regarding the quality control substance may be transmitted, for example, daily. The transmission timing of the measurement result regarding the quality control substance may be set for each facility and each blood cell counter.

As shown in FIG. 3B, each of the blood cell counters 3 transmits a data set including the result of the measurement process for the subject sample to the quality control support device 1. The transmitted data set includes the device ID of the blood cell counter 3, the measurement date and time, and the measured value in association with each other. The result of the measurement process relating to the subject sample is transmitted to the quality control support device 1 when the measurement of a predetermined number (for example, 20 samples) is completed. Note that the predetermined number may be set for each facility. The data sets shown in FIGS. 3A and 3B transmitted from each of the blood cell counters 3 are stored in the storage device 13 of the quality control support device 1.

The data sets shown in FIGS. 3A and 3B contain information regarding at least one of error occurrence in the blood cell counter 3, calibration of the blood cell counter 3, or reagent exchange of the blood cell counter 3. The information regarding the occurrence of an error in the blood cell counter 3 includes, for example, the date and time of the occurrence of the error and the content of the error. The information regarding the execution of the calibration of the blood cell counter 3 includes, for example, the date and time of the calibration and the content of the calibration. The information regarding the reagent exchange for the blood cell counter 3 may include, for example, the reagent exchange date and time and the reagent identification information before and after the exchange. Note that the transmission format of the data set shown in FIGS. 3A and 3B is arbitrary, and may be configured in, for example, a predetermined data packet format.

Figure 4:
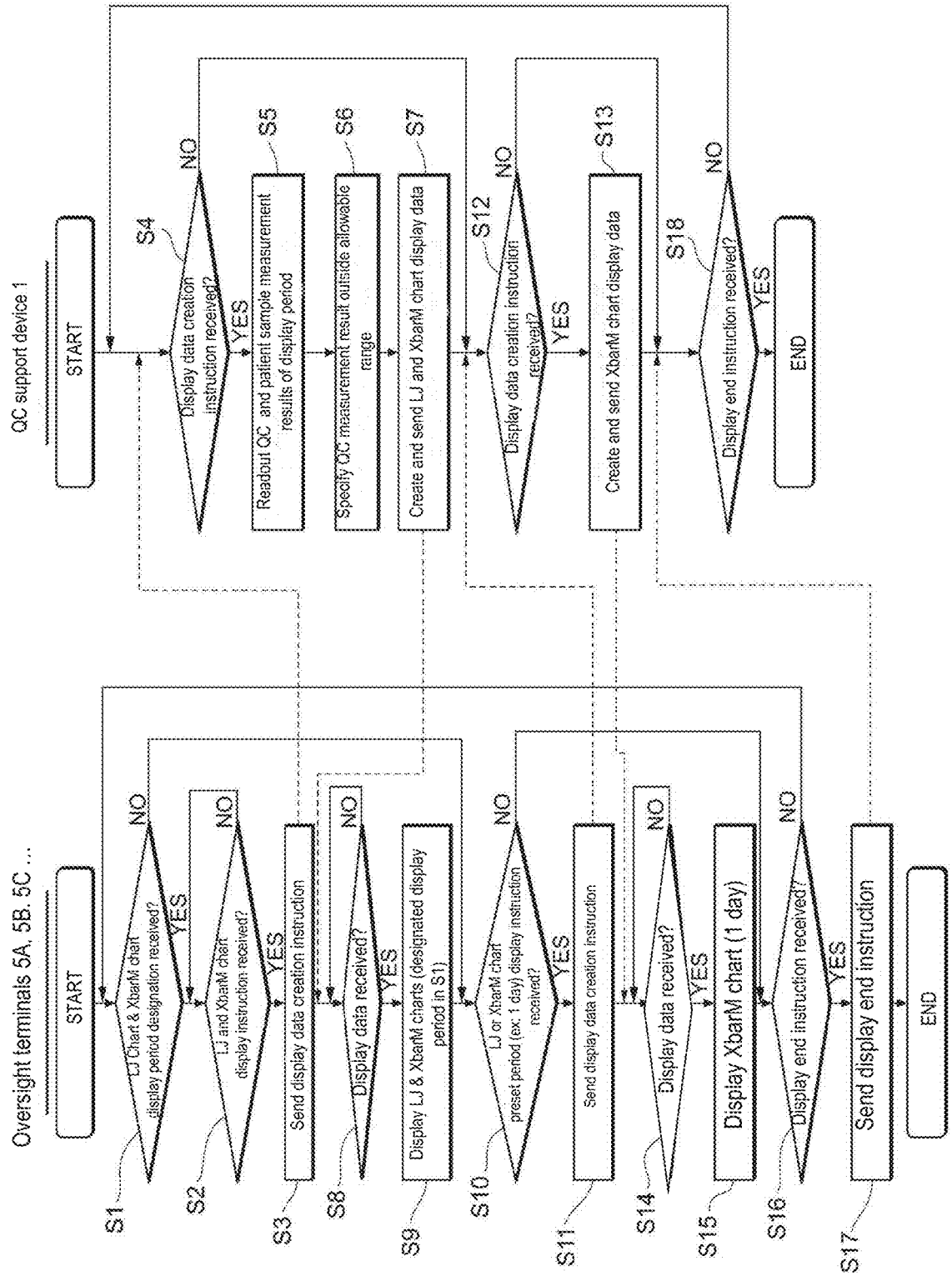
FIG. 4 is a flowchart showing an example of a QC (Quality Control) chart display process according to the first embodiment.

FIG. 4 is a flowchart showing an example of the display process of the QC chart according to the first embodiment. As shown in FIG. 4, the QC chart display process is executed between the oversight terminal 5 and the quality control support device 1. Note that, as a premise, the measurement data measured by the blood cell counter 3 at each facility are transmitted to the quality control support device 1 as a part of a predetermined data set, as described with reference to FIG. 3. The quality control support device 1 stores the received measurement data in the storage device 13 shown in FIG. 2.

(Step S1)

The processor 11 of the oversight terminal 5 operated by the person in charge of the facility (hereinafter, simply referred to as the oversight terminal 5) determines whether a designation related to the display period of the QC chart (for example, the LJ chart and the XbarM chart) to be displayed on the quality control support device 1 has been received from the person in charge. If the designation is received (YES in step S1), the process proceeds to step S2, whereas if the designation is not received (NO in step S1), the process proceeds to step S10. Here, the LJ chart is a control chart showing the results of measuring the quality control substances in time series, and the XbarM chart is a control chart showing the results of measuring the subject samples in time series.

One display period is specified as the display period of the LJ chart and the XbarM chart. For example, if the display period of the LJ chart is specified from Dec. 27, 2019 to Jan. 5, 2020, both the LJ chart and the XbarM chart will be displayed for the period from Dec. 7, 2019 to Jan. 5, 2020. That is, the display period of the LJ chart is automatically set to the display period of the XbarM chart.

(Step S2)

The oversight terminal 5 determines whether the person in charge has received the display instruction of the LJ chart and the XbarM chart. If the designation is received (YES in step S2), the process proceeds to step S3, whereas if the designation is not received (NO in step S2), the process waits until the designation is received.

(Step S3)

The oversight terminal 5 transmits the display data creation instruction to the quality control support device 1 based on the received display instruction.

(Step S4)

The processor 11 of the quality control support device 1 (hereinafter, simply referred to as the quality control support device 1) determines whether a display data creation instruction has been received from the oversight terminal 5. If the instruction is received (YES in step S4), the process proceeds to step S5, whereas if the instruction is not received (NO in step S4), the process proceeds to step S12.

(Step S5)

The quality control support device 1 reads out the measurement data of the blood cell counter 3 stored in advance from the storage device 13 shown in FIG. 2. For example, the quality control support device 1 reads out the QC measurement result and the subject sample measurement result in the display period corresponding to the period from Dec. 27, 2019 to Jan. 5, 2020.

(Step S6)

The quality control support device 1 identifies a QC measurement result outside the permissible range. As will be described later with reference to FIG. 5, the quality control support device 1 may specify, for example, measurement data exceeding the upper limit value 1 and measurement data below the lower limit value 1. The quality control support device 1 also may be controlled so as not to reflect the specified measurement data in the chart, for example.

(Step S7)

The quality control support device 1 generates information for displaying the LJ chart and the XbarM chart on the display provided in the oversight terminal 5, and transmits the information to the oversight terminal 5. Note that the quality control support device 1 also may display the LJ chart and the XbarM chart on the output device 16 shown in FIG. 2 included in the quality control support device 1.

(Step S8)

The oversight terminal 5 determines whether the display data for displaying the LJ chart and the XbarM chart have been received from the quality control support device 1. When the display data are received (YES in step S8), the process proceeds to step S9, whereas when the display data are not received (NO in step S8), the process waits until the display data are received.

(Step S9)

Based on the received display data, the oversight terminal 5 displays the LJ chart and the XbarM chart on the display during the display period specified in step S1 (the period corresponding to Dec. 27, 2019 to Jan. 5, 2020).

FIG. 5A is a diagram showing an example of an LJ chart. FIG. 5B is a diagram showing an example of an XbarM chart. As shown in FIGS. 5A and 5B, the oversight terminal 5 displays the LJ chart (first control chart) and the XbarM chart on the display from the display period Dec. 27, 2019 to Jan. 5, 2020.

As shown in FIG. 5A, the LJ chart is a chart in which the measurement results of the quality control substances (QC samples) measured by the blood cell counter 3 are plotted in time series. As shown in FIG. 5A, the measurement frequency of the quality control substance is one to several times per day. The "target value" (for example, "30") in the LJ chart is a reference value determined for each lot of QC samples. Each of the "upper limit value 1" and the "lower limit value 1" in the LJ chart is an upper limit value and a lower limit value determined for each lot of the QC sample. When a measurement result outside the range ("27" to "33") specified by "upper limit value 1" and "lower limit value 1" in the LJ chart is reflected in the LJ chart, identification information corresponding to "(!) Error" is added to the measurement result. Each of the "upper limit value 2" and the "lower limit value 2" in the LJ chart is a value set according to the respective values of the "upper limit value 1" and the "lower limit value 1", for example. For example, the "upper limit value 2" may be set to a value corresponding to approximately 97% of the "upper limit value 1". Each of the "upper limit value 2" and the "lower limit value 2" can be freely set by the user. If the measurement result within the range ("32" to "33") specified by "upper limit value 1" and "upper limit value 2" is reflected in the LJ chart, identification information corresponding to "(x) Warning" is added to the measurement result. If the measurement result within the range ("27" to "28") defined by "lower limit value 1" and "lower limit value 2" is reflected in the LJ chart, identification information corresponding to "(x) Warning" is added to the measurement result.

As shown in FIG. 5B, the XbarM chart is a chart created by calculating the average values of the measurement results of a predetermined number of subject samples (for example, 20 samples) received from the blood cell counter 3, and plots the average values in time series. The "target value" (for example, "8.07") in the XbarM chart is a value determined by aggregating the measurement results of past subject samples. The "target value" is provided by the service provider. The "target value" also may be a value set by the user. Each of the "upper limit value 1" and the "lower limit value 1" in the XbarM chart is an upper limit value and a lower limit value provided by the service provider. Each of the "upper limit value 1" and the "lower limit value 1" also may be a value set by the user. The "target value", "upper limit value 1", and "lower limit value 1" also may be different for each blood cell counter 3. Each of the "upper limit value 2" and the "lower limit value 2" in the XbarM chart is a value set according to the respective values of the "upper limit value 1" and the "lower limit value 1", for example. Each of the "upper limit value 2" and the "lower limit value 2" also may be a value set by the user. Note that each limit value in the XbarM chart can be omitted.

The line L1 in FIG. 5A is displayed so as to pass through the QC measurement point MP1 closest to the mouse cursor C1 when the mouse cursor C1 is displayed on the LJ chart. Note that instead of displaying the line L1, for example, the area corresponding to one day (24 hours) including the QC measurement point MP1 may be displayed. When the user aligns the mouse cursor C1 (when the display displaying the LJ chart is a touch panel, a touch pen, the user's finger or the like) on the line L1 and moves the line L1 in the left-right direction, the display position of the line L1 Is changed. Regarding one day including the line L1 (a part of the area of the first control chart) on the LJ chart shown in FIG. 5A (in the example of FIG. 5A, Jan. 3, 2020), the specific area A1 is displayed on the XbarM chart shown in FIG. 5B. When the line L1 on the LJ chart is moved in the left-right direction, the specific area A1 on the XbarM chart (third control chart) also moves following the left-right direction. That is, the display form of the XbarM chart is changed according to the change of the line L1 on the LJ chart.

(Step S10 in FIG. 4)

Returning to FIG. 4, the oversight terminal 5 determines whether a display instruction has been received from the person in charge for a predetermined period (for example, one day) (second period) on the XbarM chart or the LJ chart via the pointing device. If an instruction is received (YES in step S10), the process proceeds to step S11, whereas if an instruction is not received (NO in step S10), the process proceeds to step S16.

(Step S11)

The oversight terminal 5 transmits a display data preparation instruction corresponding to the received display instruction to the quality control support device 1.

(Step S12)

The quality control support device 1 determines whether a display data preparation instruction corresponding to the display instruction received by the oversight terminal 5 has been received. If the instruction is received (YES in step S12), the process proceeds to step S13, whereas if the instruction is not received (NO in step S12), the process proceeds to step S18.

(Step S13)

The quality control support device 1 creates display data for displaying the XbarM chart (second control chart) in the above day corresponding to the received instruction, and transmits the data to the oversight terminal 5.

(Step S14)

The oversight terminal 5 determines whether the display data for displaying the XbarM chart (second control chart) has been received from the quality control support device 1. When the display data are received (YES in step S14), the process proceeds to step S15, whereas when the display data are not received (NO in step S14), the process waits until display data are received.

(Step S15)

The oversight terminal 5 displays the XbarM chart (second control chart) based on the received display data.

(Step S16)

The oversight terminal 5 determines whether the display end instruction has been received from the person in charge. If the instruction is received (YES in step S16), the process proceeds to step S17, whereas if the instruction is not received (NO in step S16), the process returns to step S1.

(Step S17)

The oversight terminal 5 transmits an instruction to end the display to the quality control support device 1 and ends the process.

(Step S18)

The quality control support device 1 determines whether a display end instruction has been received from the person in charge terminal 5. When the end instruction is received (YES in step S18), the process ends, whereas when the end instruction is not received (NO in step S18), the process returns to step S4.

First Example

Figure 6A:
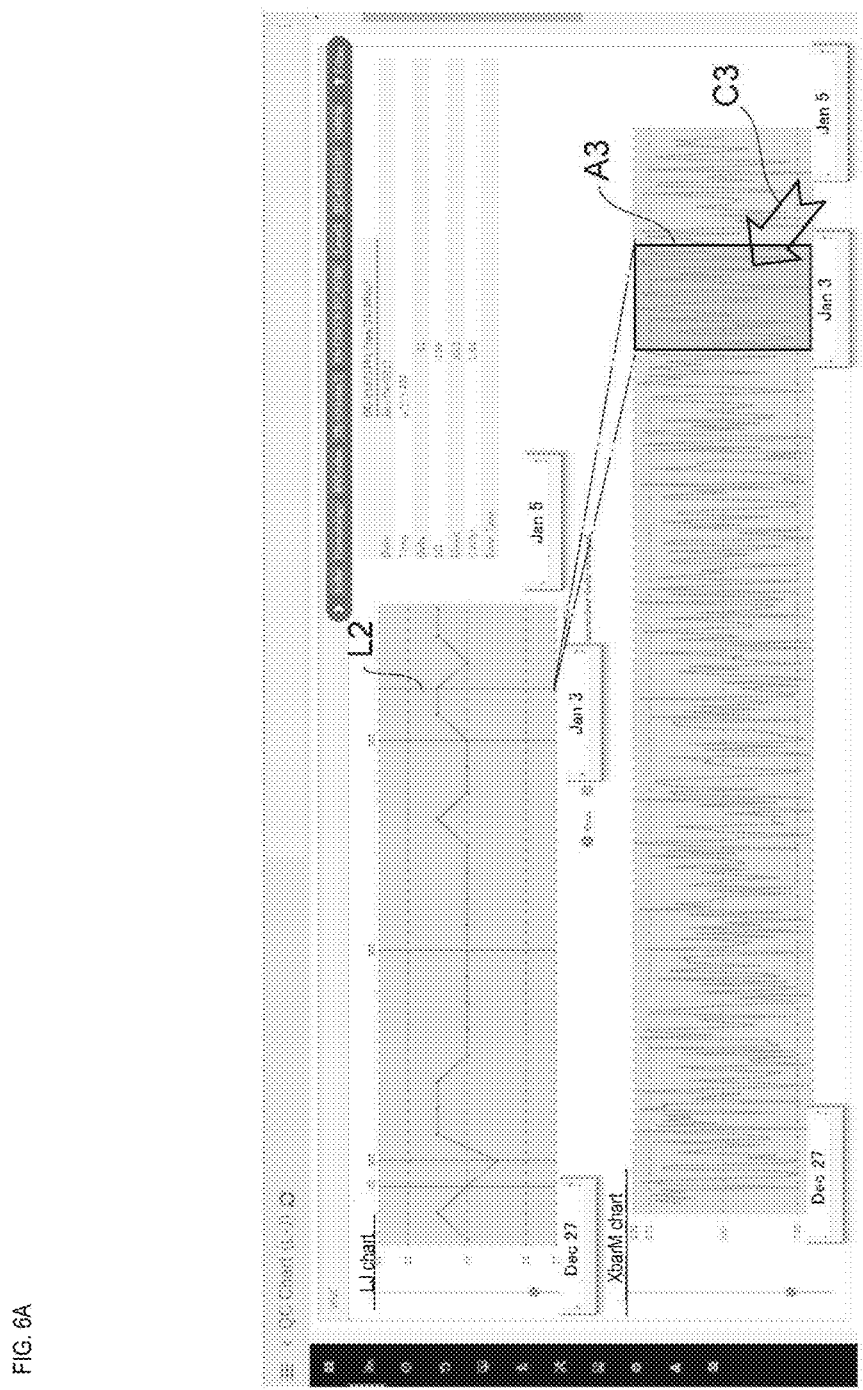
FIG. 6A is a diagram showing an example of an LJ chart and XbarM chart.

FIG. 6A is a diagram showing examples of an LJ chart and an XbarM chart. FIG. 6B is a diagram showing an example of an XbarM chart. The FIG. 6A show an example of a LJ chart (first control chart) displayed on the display of the oversight terminal 5 during the display period (first period) from Dec. 27, 2019 to Jan. 5, 2020, and displays an XbarM chart (third control chart) during the display period (third period) from Dec. 27, 2019 to Jan. 5, 2020. When the line L2 on the LJ chart shown in FIG. 6A is specified (a part of the area of the first control chart is specified), the specific area A3 (a part of the area of the third control chart) on the XbarM chart corresponding to the above one day (Jan. 3, 2020) is displayed in a form different from the other areas. On the XbarM chart, the specific area A3 and the other areas may be displayed in different colors, or only the specific area A3 may be highlighted. Here, when the person in charge operates the cursor C3 and selects the specific area A3 corresponding to Jan. 3, 2020 (designates a part of the area of the third control chart), the XbarM chart (second control chart) of FIG. 6B showing the results of measuring the subject sample with the blood cell counter 3 is displayed in the period corresponding to Jan. 3, 2020 (second period), which is shorter than the period corresponding to Dec. 27, 2019 to Jan. 5, 2020 (third period). According to this configuration, the LJ chart (first control chart) and the XbarM chart (second control chart) are displayed in the display period according to the difference between the measurement frequency of the quality control substance and the measurement frequency of the subject sample. Accordingly, the cause can be easily identified when there is an abnormality in the measurement result.

For example, although it is difficult to grasp the fluctuation of the measurement results of the subject sample on Jan. 3, 2020 due to the short interval between the measurement results in the XbarM chart (third control chart) shown in FIG. 6A, the fluctuation of the measurement results of the subject sample in one day can be easily grasped in the XbarM chart (second control chart) of the second period shown in FIG. 6B.

According to this configuration, an XbarM chart (second control chart) is displayed for any one day desired by the viewer. Therefore, it becomes possible to confirm the measurement result on the day when the abnormality occurs, and it becomes easier to identify the cause of the abnormality.

According to this configuration, the display period of the LJ chart (first control chart) is received and the LJ chart (first control chart) is displayed for the received display period, such that, for example, the QC samples can be traced back to the past and it becomes easy to grasp the fluctuation of the measurement results of the sample since the LJ chart (first control chart) is displayed for the received display period. Therefore, it becomes easier to identify the cause of an abnormality.

According to this configuration, since the designation of the display period of the XbarM chart (second control chart) shown in FIG. 6B is received while the LJ chart (first control chart) is displayed on the display, the time at which an abnormality occurs can be estimated via the LJ chart (first control chart) and it is possible to confirm the fluctuation of the estimated occurrence time in detail from the XbarM chart (second control chart) shown in FIG. 6B. Therefore, it becomes easier to identify the cause of an abnormality.

According to the configuration, since the XbarM chart (second control chart) shown in FIG. 6B is displayed by displaying the XbarM chart (third control chart) shown in FIG. 6A on the display and receiving the designation of the of the specific area A3 of the XbarM chart (third control chart) shown in FIG. 6A, with regard to the fluctuation of the measurement result of the subject sample, it becomes possible to confirm both the fluctuation in the medium- to long-term and the fluctuation in the short-term, and it becomes easier to estimate the time when the cause of the abnormality occurs. Therefore, it becomes easier to identify the cause of an abnormality. According to this configuration, since the specific area A1 indicating the period corresponding to the line L1 displayed on the LJ chart (first control chart) shown in FIG. 6A is displayed in a mode different from that of other periods in the XbarM chart (third control chart) shown in FIG. 6A, it becomes easy to confirm the measurement result of the subject sample at the time when the measurement result of the QC sample is abnormal. Therefore, it becomes easier to estimate the time when the cause of the abnormality occurs. Since the specific area A1 moves following the movement of the line L1, it becomes easy to specify the display period of the XbarM chart (second control chart) shown in FIG. 6B.

Second Example

Figure 7:
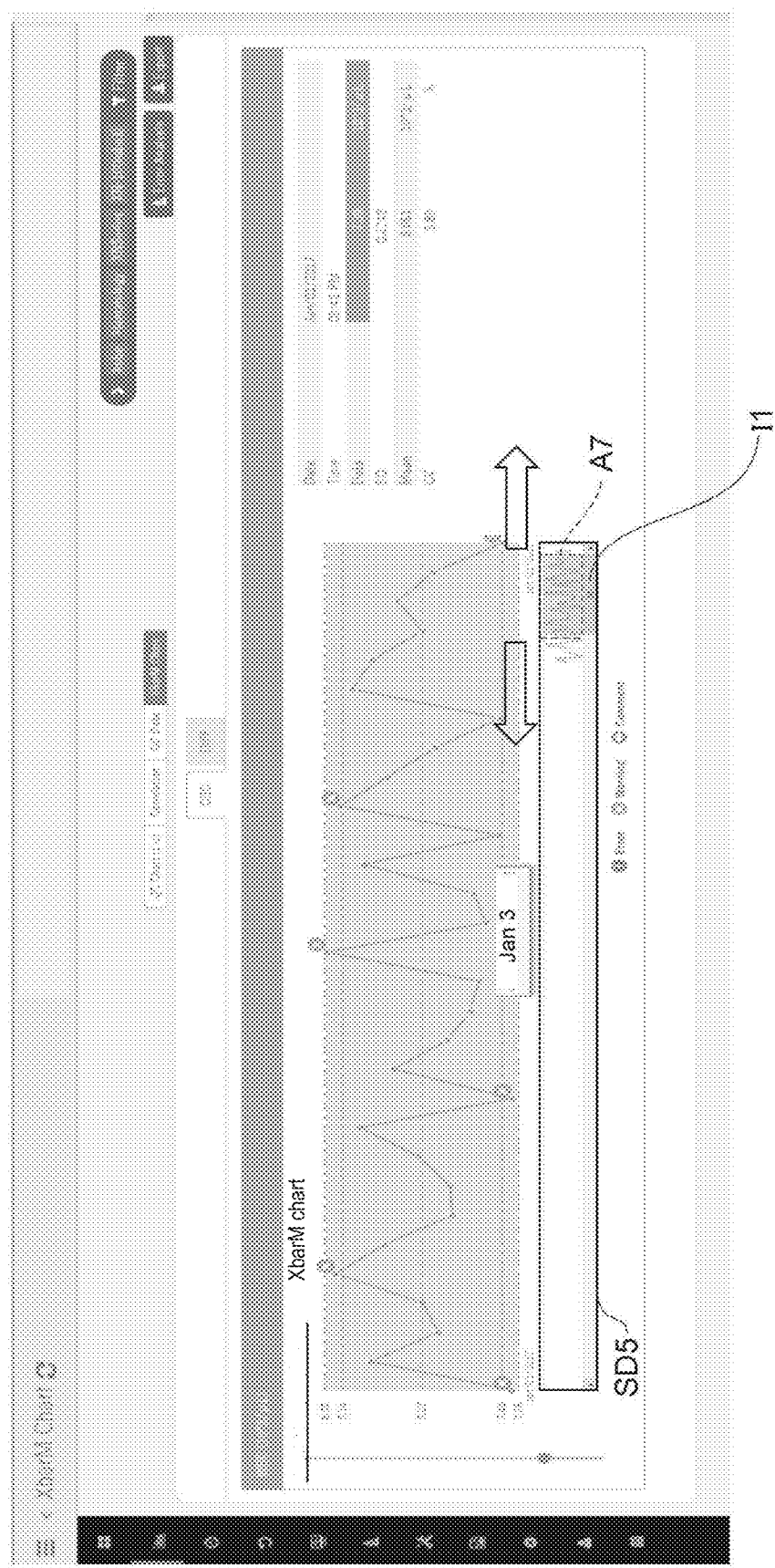
FIG. 7 is a diagram showing an example of an XbarM chart according to the first embodiment.

FIG. 7 is a diagram showing an example of an XbarM chart according to an embodiment. In the indicator screen SD5 shown in FIG. 7, the XbarM chart (second control chart), which has a display period of 1 day (in this example, Jan. 3, 2020) shown in FIG. 7, is a screen showing which display period corresponds to the display period from Dec. 27, 2019 to Jan. 5, 2020 of the XbarM chart (third control chart) shown in FIG. 6A. That is, in the display of the XbarM chart shown in FIG. 7, the indicator screen SD5 is a relationship screen displaying the relationship between the display period (second period: Jan. 3, 2020 in this example) and a display period of the XbarM chart shown in FIG. 6A (third period: Dec. 27, 2019 to Jan. 5, 2020 in the example).

The change of the display period of the XbarM chart shown in FIG. 7 is received via the display on the oversight terminal 5 on which the indicator screen SD5 is displayed (the position of the specific area A7 is changed by moving the indicator I1 to the left or right), and the display period of the XbarM chart is changed according to the received change.

According to this configuration, since the relationship between the display period of the XbarM chart (third control chart) shown in FIG. 6A and the display period of the XbarM chart (second control chart) shown in FIG. 7 becomes readily understood, regarding the fluctuation of the measurement result of the subject sample, it becomes possible to confirm both the fluctuation in the medium- to long-term and the fluctuation in the short-term, and becomes easier to estimate the time when the cause of the abnormality occurs.

According to this configuration, since the display period of the XbarM chart (second control chart) shown in FIG. 7 can be changed, it becomes possible to confirm the short-term fluctuation of the measurement result in a plurality of periods, and becomes easier to estimate the time when the cause of the abnormality occurs.

Third Example

Figure 8A:
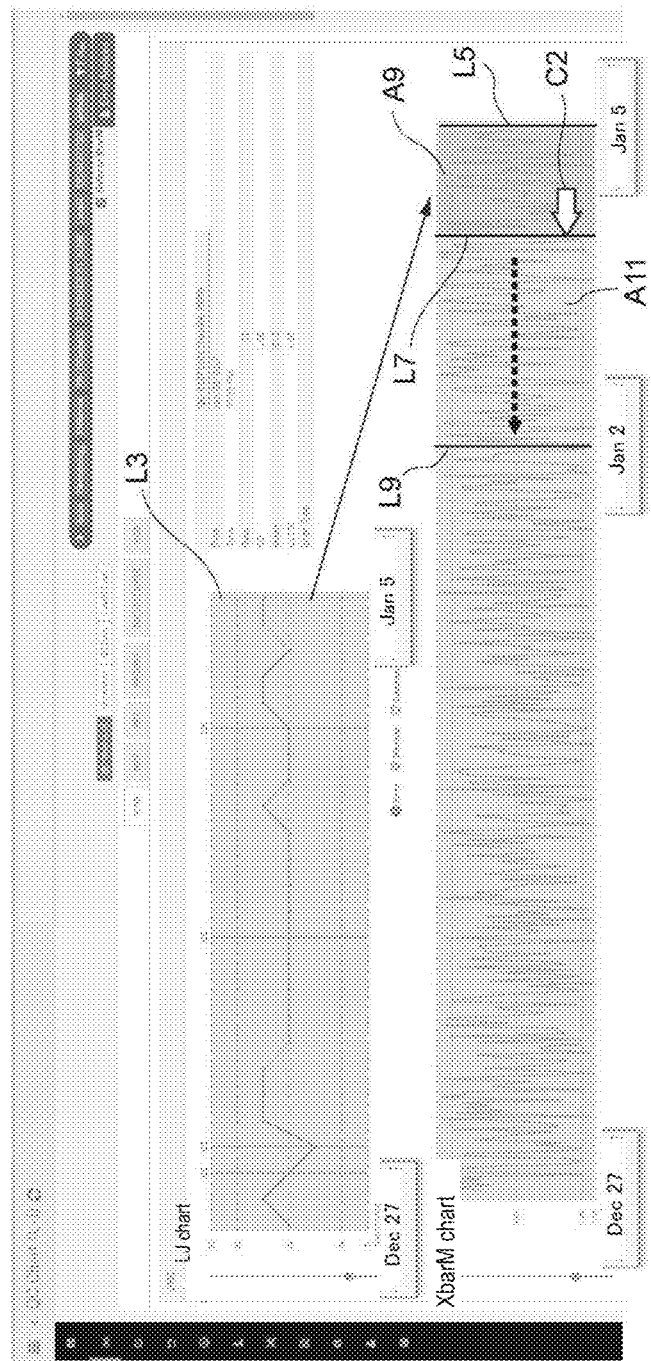
FIG. 8A is a diagram showing an example of an LJ chart and an XbarM chart.
Figure 8C:
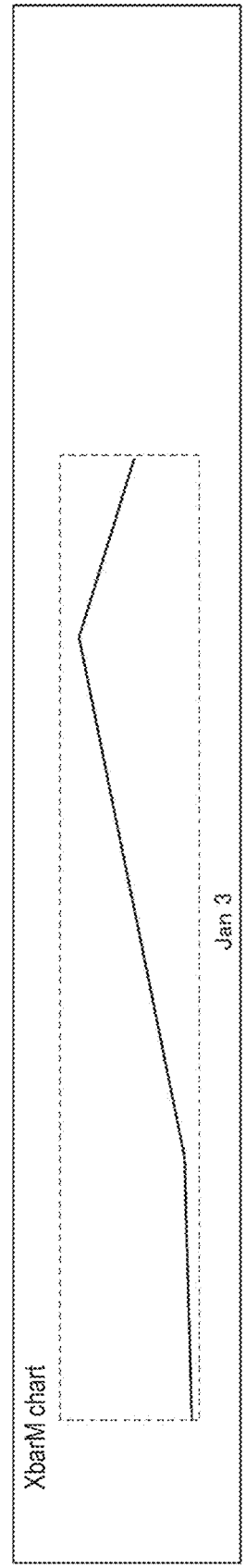
FIG. 8C is a diagram showing an example of an XbarM chart displayed when a predetermined operation is executed in the XbarM chart of FIG. 8B.

FIG. 8A is a diagram showing an example of an LJ chart and an XbarM chart. FIG. 8B is a diagram showing an example of an XbarM chart (second control chart) displayed when a predetermined operation is executed in the XbarM chart of FIG. 8A. FIG. 8C is a diagram showing an example of an XbarM chart (second control chart) displayed when a predetermined operation is executed in the XbarM chart of FIG. 8B. In FIG. 8A, the LJ chart (first control chart) is displayed on the display of the oversight terminal 5 during the display period (first period) from Dec. 27, 2019 to Jan. 5, 2020, and an example is shown in which the XbarM chart (third control chart) is displayed during the display period (third period) from Dec. 27, 2019 to Jan. 5, 2020. When the line L3 on the LJ chart shown in FIG. 8A is specified, the specific area A9 on the XbarM chart corresponding to one day (Jan. 5, 2020) including the line L3 is displayed in a form different from the other areas. The specific area A9 is an area defined by the line L5 and the line L7 on the XbarM chart. Here, when the person in charge operates the cursor C2 to move the line L7 on the XbarM chart to the position of the line L9 corresponding to Jan. 2, 2020, the line L9 and the line L5 are displayed on the XbarM chart and a new defined region A11 is formed. When the person in charge selects the specific area A11 (designates a part of the area in the third control chart), the results of measuring the subject samples with the blood cell counter 3 during the period from Jan. 2, 2020 to Jan. 5, 2020 are shown, and the XbarM chart (second control chart) shown in FIG. 8B is displayed. When the person in charge selects the specific region A13 corresponding to January 3, the results of measuring the subject samples with the blood cell counter 3 in the period corresponding to Jan. 3, 2020 is shown, and the XbarM chart (second control chart) shown in FIG. 8C is displayed.

Fourth Example

Figure 9:
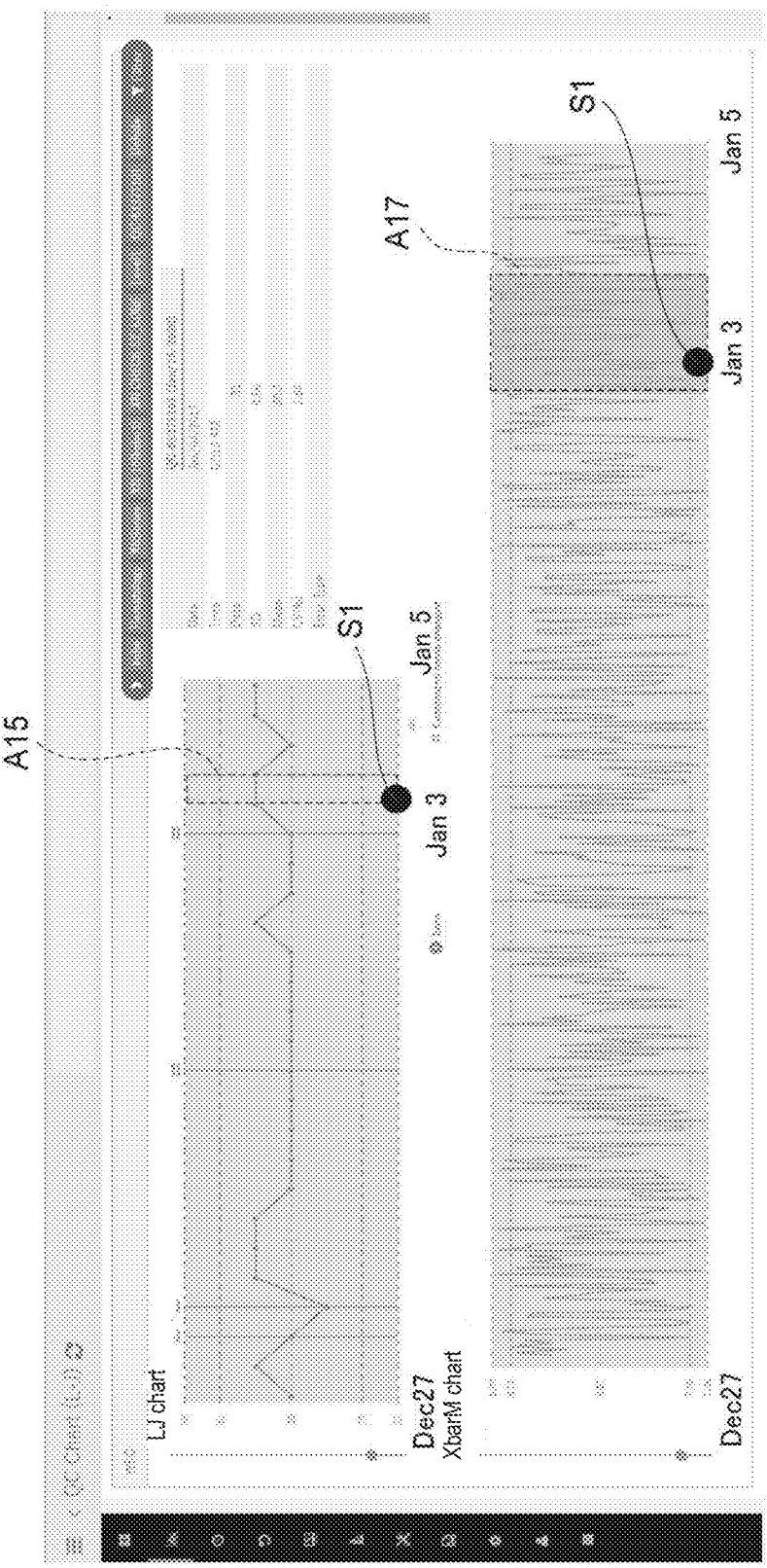
FIG. 9 is a diagram showing an example of an LJ chart and an XbarM chart.
Figure 10:
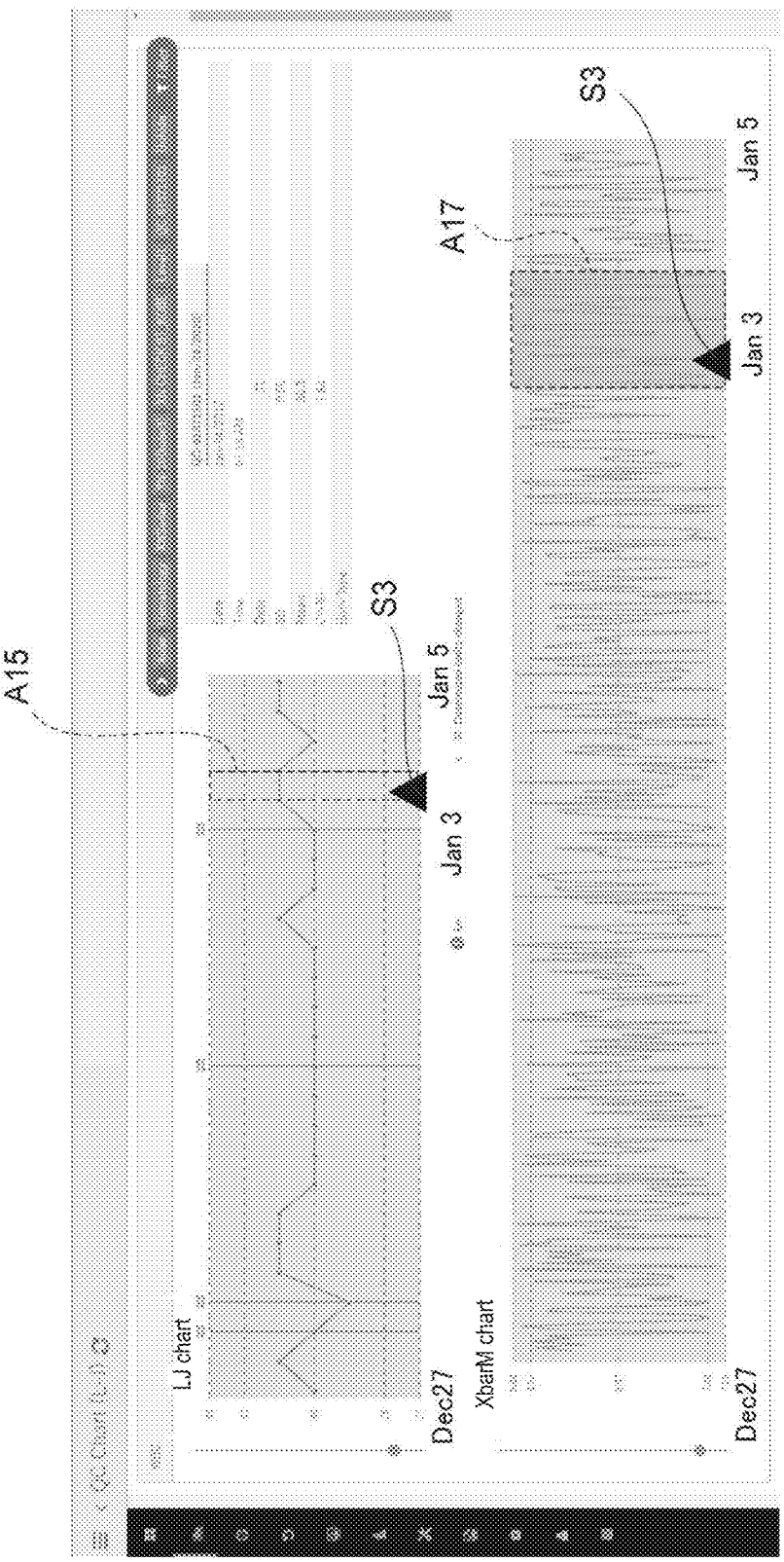
FIG. 10 is a diagram showing another example of the LJ chart and the XbarM chart.
Figure 11:
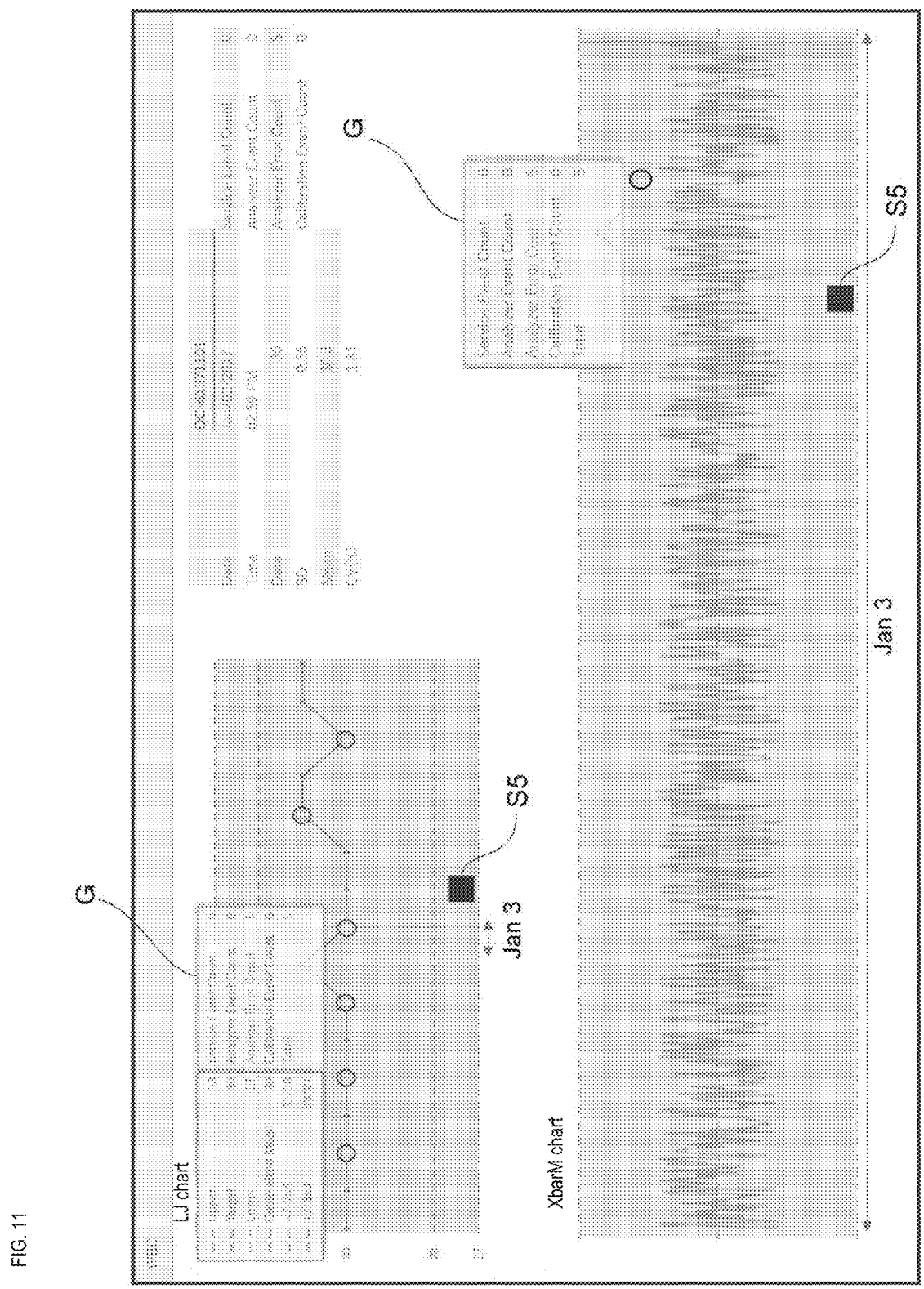
FIG. 11 is a diagram showing an example of an LJ chart and an XbarM chart according to the first embodiment.

FIGS. 9 and 10 are diagrams showing an example of the LJ chart and the XbarM chart according to the embodiment. FIG. 9 is a diagram showing an example of an LJ chart and an XbarM chart when calibration is performed during the display period. FIG. 10 is a diagram showing another example of the LJ chart and the XbarM chart when the reagent is exchanged in the blood cell counter 3 during the display period. FIG. 11 is a diagram showing an example of an LJ chart and an XbarM chart when an error occurs in the blood cell counter 3 during the display period. As shown in FIGS. 9 to 11, when a predetermined event occurs within the display period in the display of the LJ chart and the XbarM chart, a mark indicating the occurrence of the predetermined event is displayed. A predetermined event includes at least one of error occurrence in the blood counter 3, calibration of the blood counter 3, or reagent exchange of the blood cell counter 3. Before and after such an event occurs, the measurement result is more likely to become abnormal than at other times such that by displaying a mark indicating the occurrence of a predetermined event, it is easy to estimate the time when the abnormality occurs. Note that the mark indicating the occurrence of a predetermined event also may be displayed on the XbarM chart (second control chart) for which the display period is shorter than that of the LJ chart, which is shown in FIG. 6B.

As shown in FIG. 9, when the blood cell counter 3 is calibrated during the display period, the mark ● (black circle) S1 is displayed at the position corresponding to the date and time of the calibration (Jan. 3, 2020). The implementation date and time (Jan. 3, 2020) corresponds to the specific area A15 on the LJ chart and corresponds to the specific area A17 on the XbarM chart. Calibration is performed to confirm that the blood cell counter 3 outputs the optimum measurement result.

As shown in FIG. 10, when the reagent of the blood cell counter 3 is exchanged during the display period, the mark ▲ (black triangle) S3 is displayed at the position corresponding to the date and time (Jan. 3, 2020). The implementation date and time (Jan. 3, 2020) corresponds to the specific area A15 on the LJ chart and corresponds to the specific area A17 on the XbarM chart.

As shown in FIG. 10, when an error occurs in the blood cell counter 3 during the display period, the mark S5 is displayed at a position corresponding to the date and time of occurrence (Jan. 3, 2020). When the mark ■ is selected on the display of the oversight terminal 5, an image G showing a history of error occurrence (predetermined event) also may be displayed on the display. According to this configuration, the history of error occurrence can be easily grasped on the LJ chart or the XbarM chart. The marks indicating the occurrence of the predetermined event shown in FIGS. 9, 10, and 11 are displayed based on the data set described in FIG. 3. The data set contains information on calibration, reagent exchange, and error occurrence in association with their occurrence date, and the indicator indicating the occurrence of a predetermined event is displayed at the position corresponding to the occurrence date and time.

(Modification Example 1 of QC Chart Display Processing)

In the examples of FIGS. 6A and 8A, both the LJ chart and the XbarM chart are displayed, but in the modified example 1 of the QC chart display process, the quality control support device 1 first displays the LJ chart, and thereafter displays the XbarM chart according to the operation of the person in charge.

Figure 12:
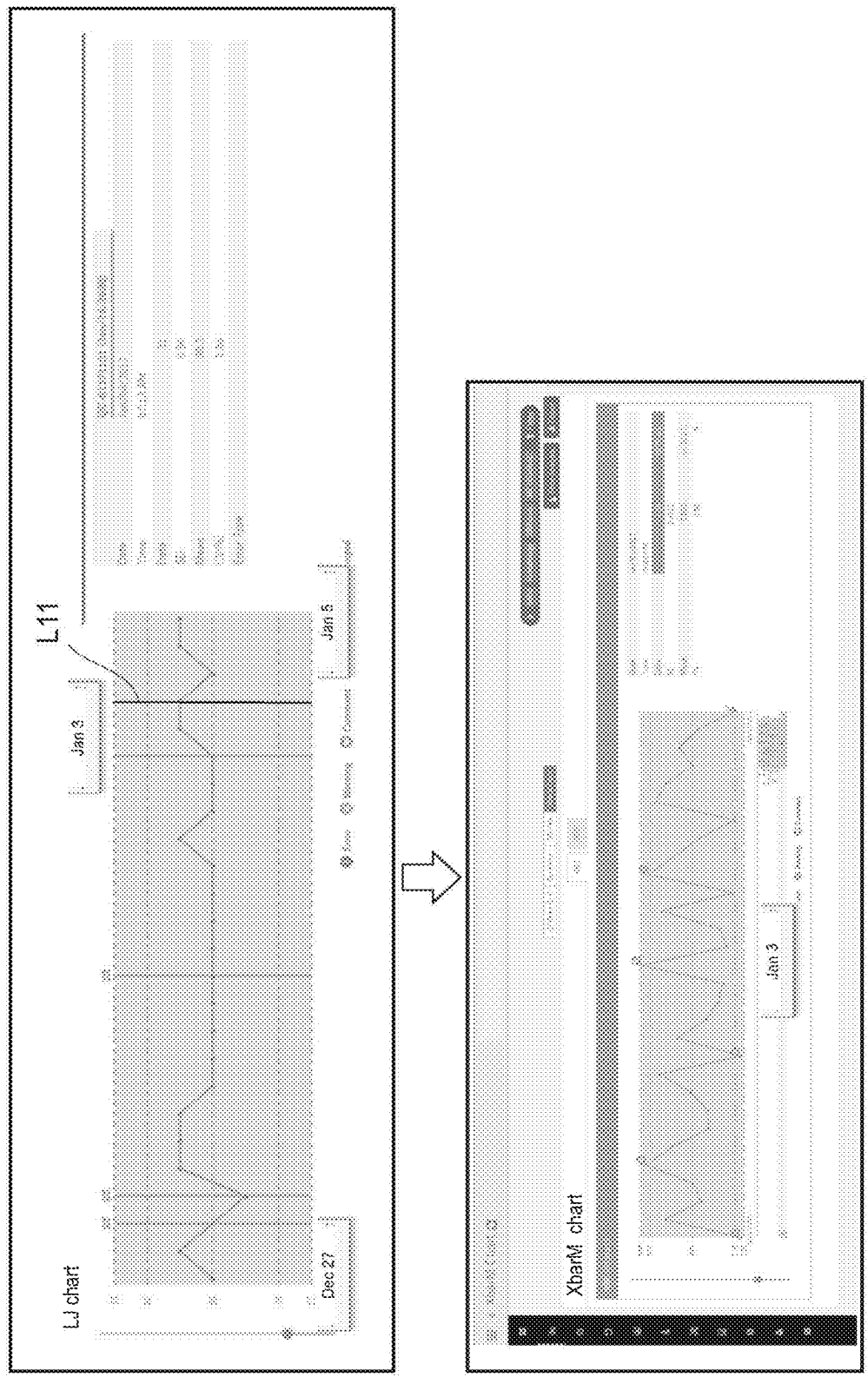
FIG. 12 is a diagram showing another example of a display process of the LJ chart and the XbarM chart according to the first embodiment.

FIG. 12 is a diagram showing another example of the display process of the LJ chart and the XbarM chart according to the embodiment. As shown in FIG. 12, the LJ chart (first control chart) is first displayed on the display of the oversight terminal 5 shown in FIG. 1. When the line L11 (a part of the area of the first control chart) corresponding to the measurement date (Jan. 3, 2020) on the LJ chart is specified, the XbarM chart (second control chart) having Jan. 3, 2020 as the display period (second period) corresponding to the designated line L11 is displayed on the display on the oversight terminal 5.

According to this configuration, since the XbarM chart with the period corresponding to line L11 as the display period (second period) is displayed by designating the line L11 corresponding to the measurement date (Jan. 3, 2020) on the LJ chart, it is possible to confirm the fluctuation of the measurement results of the subject in a short period of time with a small number of steps. Therefore, the cause of the abnormality can be identified more quickly.

(Modification 1 of Display Processing of Designated Area)

A modified example of the display processing of the line L1 of FIG. 5A, the line L2 of FIG. 6A, and the line L3 of FIG. 8A (hereinafter referred to as a designated area) will be described below. In the first modification, an example of arranging the designated area at the time of measurement or at the time of occurrence of a predetermined event will be described first. In the first modification, the designated areas are displayed in the following priority order of (1) to (4).

(1) If an error occurs in the blood cell counter 3 or if a QC measurement result warning (Warning) occurs, the designated area is displayed at the time of occurrence (point). In the case of multiple points, the specified area is displayed on the point with the largest deviation from the target value.
(2) If there is a calibration result of the blood cell counter 3, the designated area is displayed on the point.
(3) When the reagent of the blood cell counter 3 is exchanged, the designated area is displayed on the point.
(4) If (1) to (3) do not apply, the designated area is displayed on the latest data plot on the LJ chart.

(Modification 2 of Display Process of Specified Area)

Figure 13:
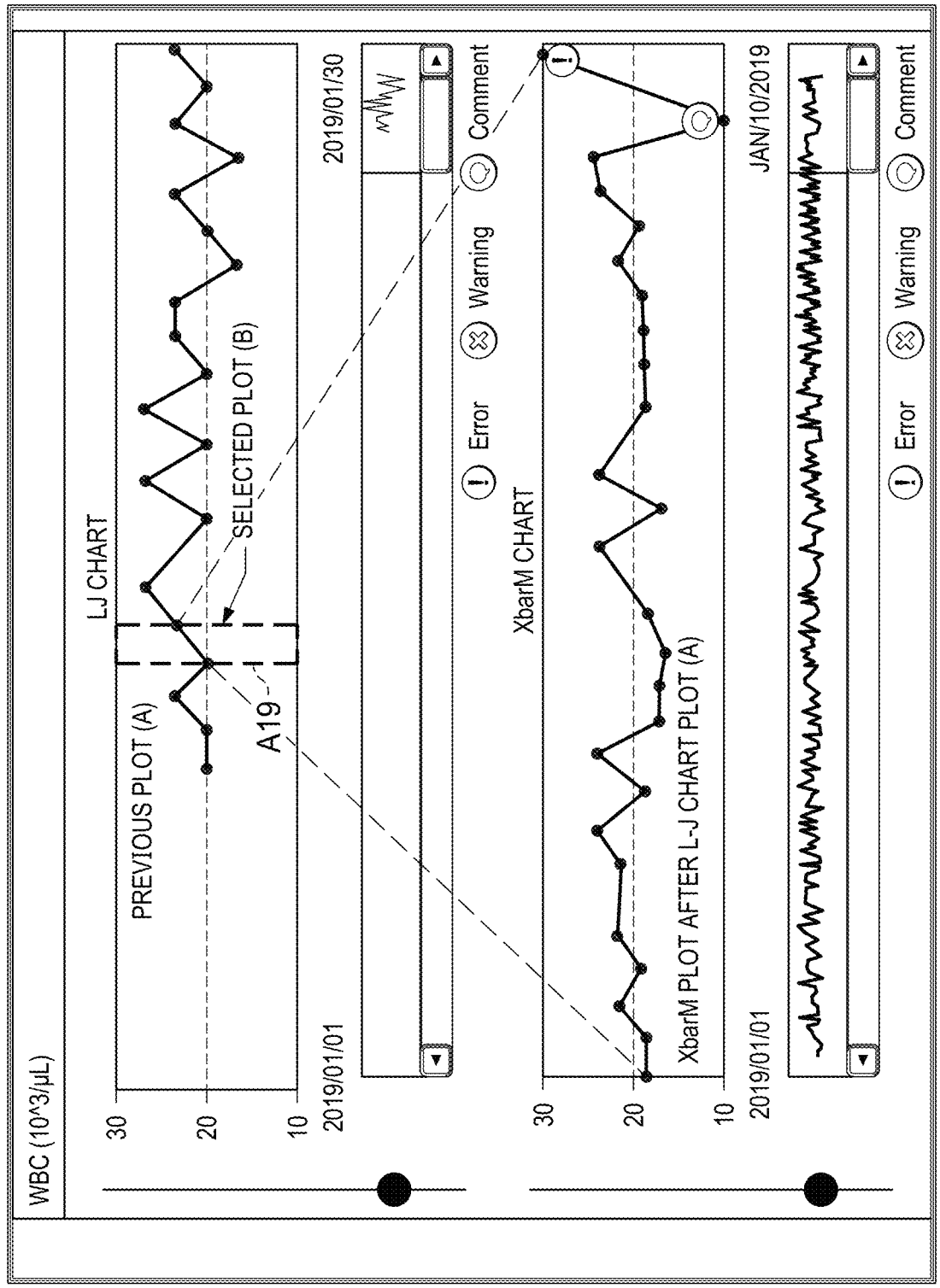
FIG. 13 is a diagram showing another example of the display form of the LJ chart and the XbarM chart according to the first embodiment.

FIG. 13 is a diagram showing another example of the display form of the LJ chart according to the embodiment. The designated area is not a line shape like the line L1 of FIG. A, the line L2 of FIG. 6A, and the line L3 of FIG. 8A, rather the LJ chart as shown in FIG. 13 may be displayed in the designated area A19 having a predetermined polygonal shape (for example, a quadrangular shape).

(Modification 3 of Display Process of Designated Area)

In the third modification, the quality control support device 1 executes the designation of the area on the LJ chart on the area designation screen.

Figure 14A:
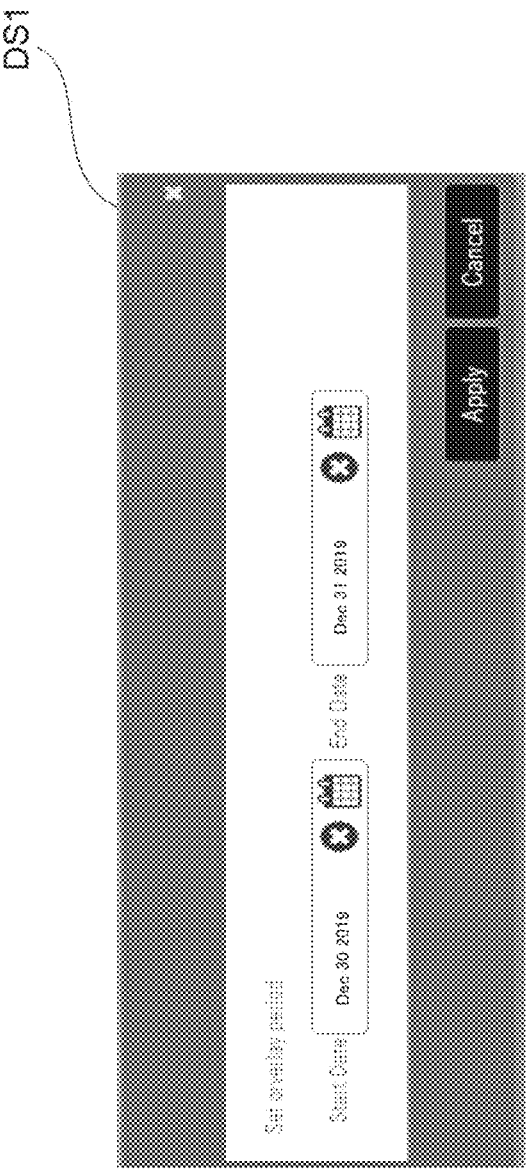
FIG. 14A is a diagram showing an example of a display period designation screen of the XbarM chart.

FIG. 14A is a diagram showing an example of the designated area designation screen DS1. FIG. 14B is a diagram showing an example of an LJ chart in which a period corresponding to a period designated on the designated area setting screen DS1 is displayed as a designated area. On the designated area setting screen DS1 shown in FIG. 14A, the display period of the designated area on the LJ chart is designated from Dec. 30, 2019 to Dec. 31, 2019. In this case, as shown in FIG. 14B, the LJ chart including the designated area A21 starting from Dec. 30, 2019 and ending on Dec. 31, 2019 is displayed.

(Modification Example 4 of Display Process of Designated Area)

In the modification 4, the quality control support device 1 executes control of the display size of the designated area on the LJ chart or control of the display position.

FIG. 15A is an example showing size control of a designated area in the LJ chart. FIG. 15B is an example showing position control of a designated area in the LJ chart. As shown in FIG. 15A, the display size of the designated area on the LJ chart may be controlled. The person in charge executes a multi-touch screen operation on the display on the oversight terminal 5 on which the LJ chart is displayed. For example, after specifying the designated area A23 on the display, the size of the designated area A23 is controllable by moving two fingers of the person in charge so as to expand (pinch out) or shrink (pinch in) the display size of the area A23. The control of the display size of the designated area A23 also may be executed in any direction, and may be in the horizontal direction or the vertical direction. As shown in FIG. 15B, the display position of the designated area on the LJ chart also may be controlled. The person in charge may operate the cursor C9 to specify the designated area A23 and then move the designated area A23 in the left-right direction. When the display has a touch panel function, the designated area A23 may be moved in the left-right direction by a touch operation of a person in charge.

(Modification Example 1 of Display Period Specification Process)

In the first modification, the display period of the LJ chart can be specified separately from the display period of the XbarM chart, whereas the form described with reference to FIGS. 4 and 5 describes the display period of the LJ chart as automatically set to the display period of the XbarM chart.

Figure 16:
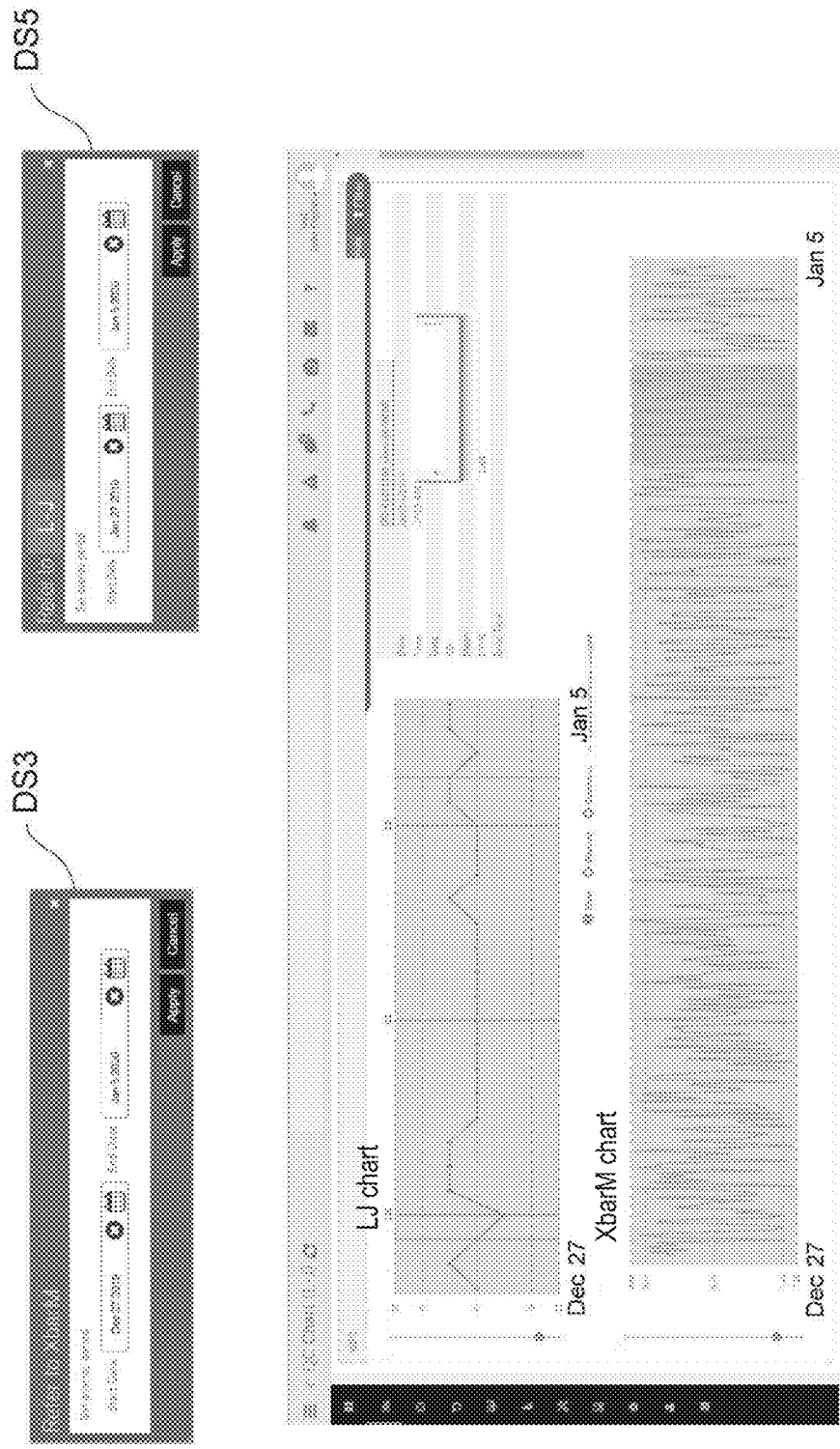
FIG. 16 is a diagram showing another example of the QC chart according to the first embodiment.

FIG. 16 is a diagram showing an example of a display period designation screen, an LJ chart, and an XbarM chart according to an embodiment. First, on the display period designation screen DS3 of the XbarM chart, the display period of the XbarM chart is designated from Dec. 27, 2019 to Jan. 5, 2020. On the display period designation screen DS5 of the LJ chart, the display period of the LJ chart is separately designated from Dec. 27, 2019 to Jan. 5, 2020. As a result, the LJ chart and the XbarM chart are displayed in the respective display periods specified via the display period designation screen DS3 and the display period designation screen DS5.

(Modification 2 of Display Period Specification Process)

Modification 2 is different from modification 1 in that the display period of the XbarM chart is set shorter than the display period of the LJ chart.

Figure 17:
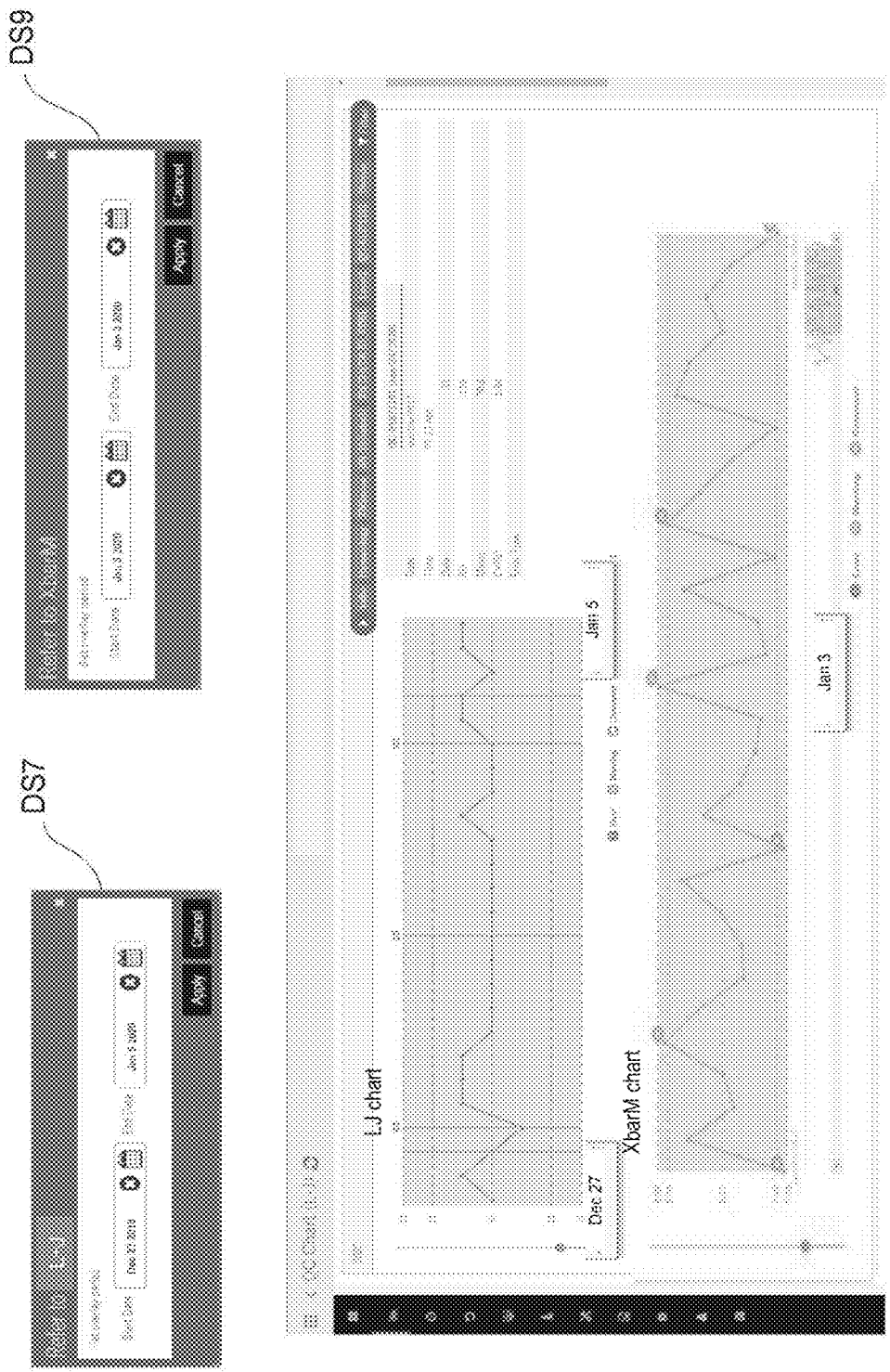
FIG. 17 is a diagram showing an example of an LJ chart and an XbarM chart according to the first embodiment, when the display period of the XbarM chart is set shorter than the display period of the LJ chart.

FIG. 17 is a diagram showing an example of a display period designation screen, an LJ chart, and an XbarM chart according to an embodiment when the display period of the XbarM chart is set shorter than the display period of the LJ chart. As shown in FIG. 17, the display period (Jan. 3, 2020), which is shorter than the period specified on the display period designation screen DS7 of the LJ chart (Dec. 27, 2019 to Jan. 5, 2020), is specified on the display period specification screen DS9 of the XbarM chart. In this case, the LJ chart displayed in the display period corresponding to the period from Dec. 27, 2019 to Jan. 5, 2020, and the XbarM chart displaying the display period corresponding to the separately specified period (Jan. 3, 2020), are displayed side by side.

According to this configuration, for example, when the time of occurrence of an abnormality can be estimated from the occurrence of an error during measurement operation, the display period of the XbarM chart can be specified on the display period specification screen DS9, so that a short period of time can be achieved with a small number of steps, thus allowing confirmation of the fluctuation of the measurement result of the subject during the period. Therefore, the cause of the abnormality can be identified more quickly.

Note that the display period of the XbarM chart display period may overlap at least partly with the display period of the LJ chart; for example, the display period of the LJ chart may be specified from Dec. 27, 2019 to 2020 to Jan. 5, 2019, and Dec. 26, 2019 to Dec. 28, 2019 may be specified as the display period of the XbarM chart.

(Modification 3 of Display Period Specification Process)

In modification 3, when a specific area is specified in the XbarM chart displayed in the predetermined display period, the display is switched to the XbarM chart in the display period corresponding to the specific area.

Figure 18:
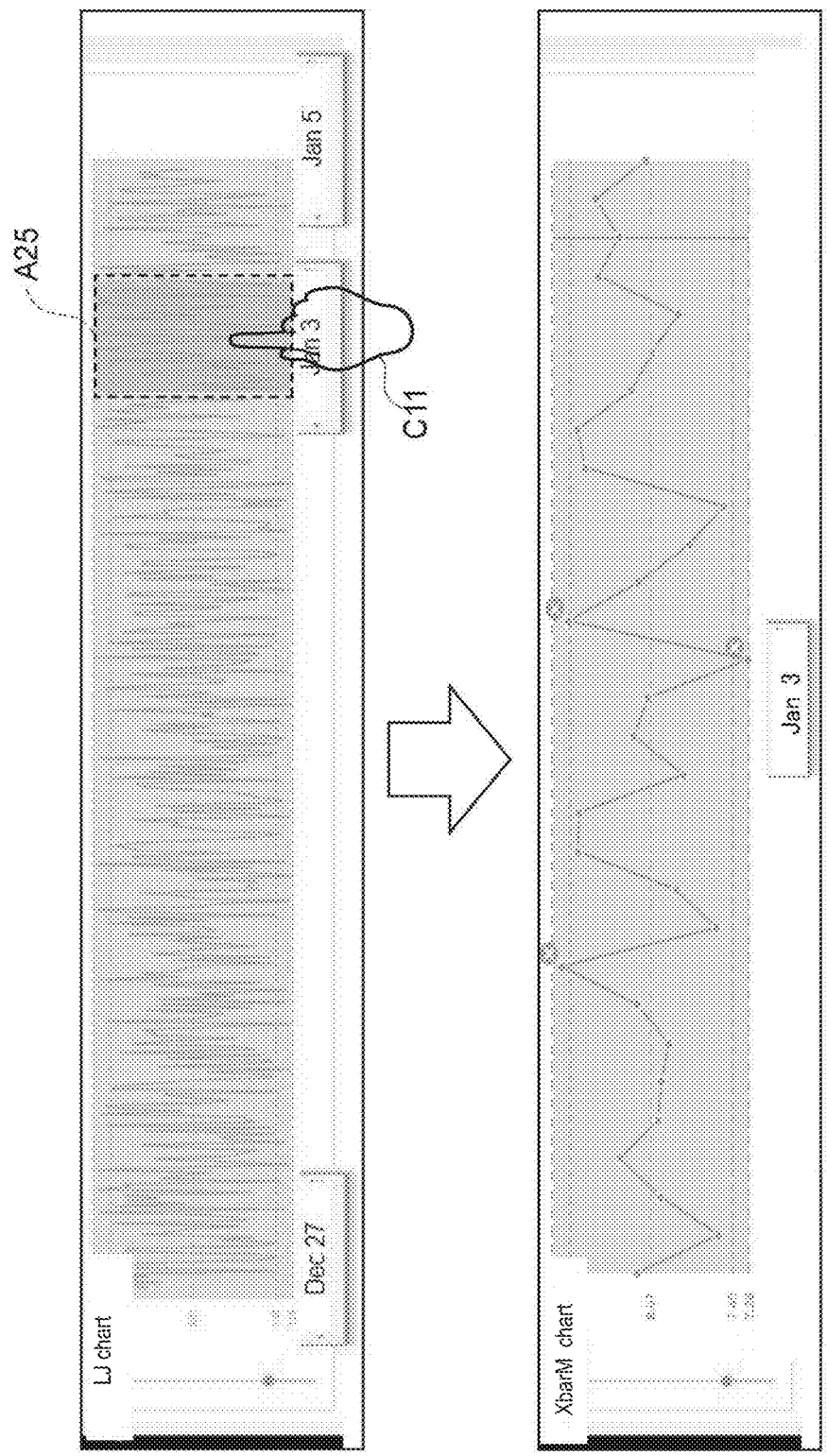
FIG. 18 is a diagram showing an example of an XbarM chart according to the first embodiment.

The upper XbarM chart in FIG. 18 is an XbarM chart displayed during the display period from Dec. 27, 2019 to Jan. 5, 2020. The specific area A25 corresponding to Jan. 3, 2020 on this XbarM chart is designated by, for example, the cursor C11.

In this case, the display is switched to the XbarM chart on the lower side of FIG. 18. The lower XbarM chart in FIG. 18 is an XbarM chart having a display period of Jan. 3, 2020 corresponding to the specific area A25.

(Modification Example 4 of Display Period Specification Process)

In the modified example 4, even if the designation of the display period is not received, the XbarM with a predetermined display period of the display period of the LJ chart (for example, the last day of the display period of the LJ chart) is displayed automatically.

Figure 19A:
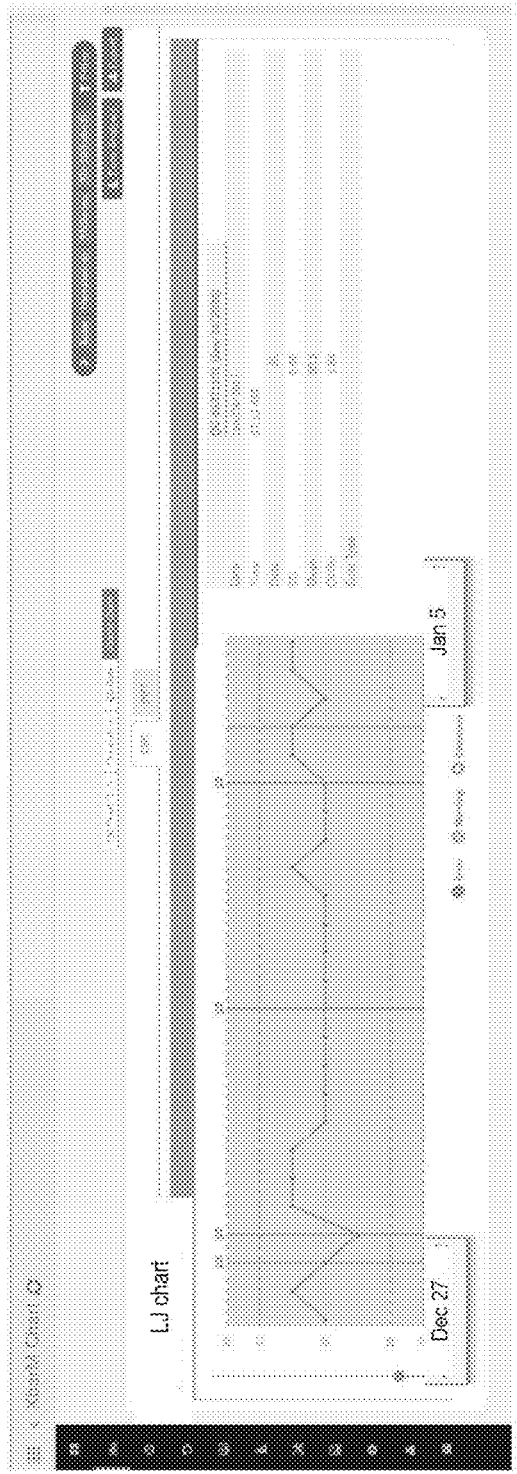
FIG. 19A is a diagram showing an example of an LJ chart displayed in a designated display period.
Figure 19B:
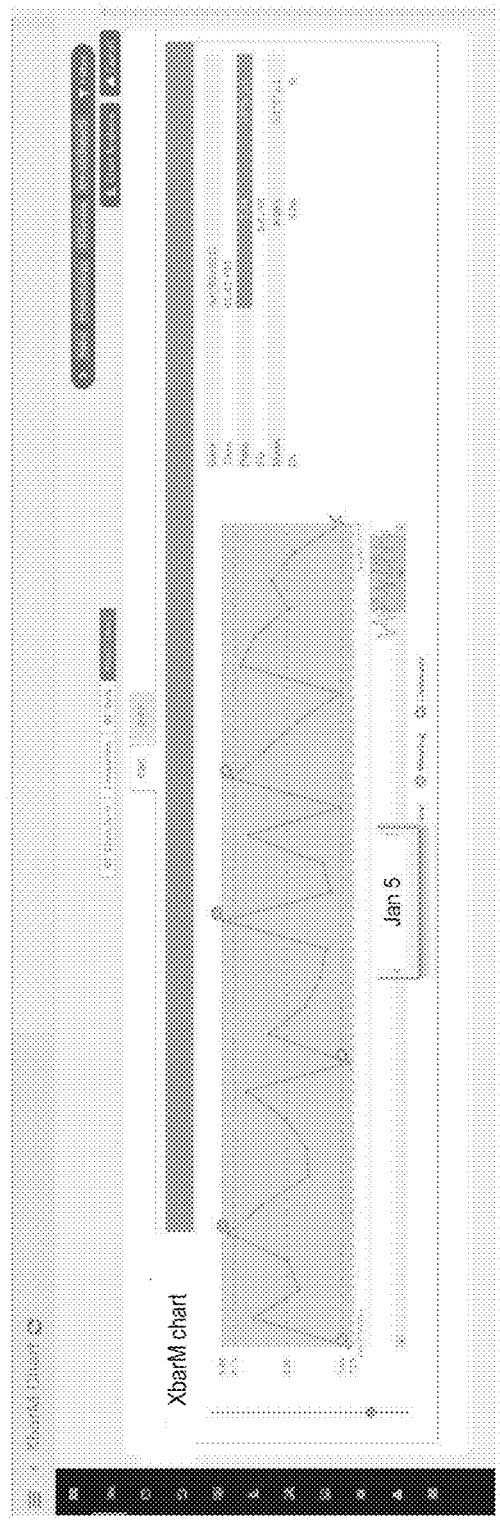
FIG. 19B is a diagram showing an example of an XbarM chart displayed in a display period corresponding to a specific period in the LJ chart of FIG. 19A.

FIG. 19A is a diagram showing an example of an LJ chart displayed in a designated display period. FIG. 19B is a diagram showing an example of an XbarM chart displayed in the display period corresponding to the last day of the display period of the LJ chart in the LJ chart of FIG. 19A. As shown in FIG. 19A, the last day on the LJ chart displayed during the display period from Dec. 27, 2019 to Jan. 5, 2020 is Jan. 5, 2020. In this case, as shown in FIG. 19B, the XbarM chart having the display period of Jan. 5, 2020 corresponding to the last day on the LJ chart is automatically displayed.

According to the first embodiment described above, the quality control support system 100 displays the first control chart (MJ chart) on the display in the first period, and the second control chart (XbarM chart) in the second period which is shorter than the first period on the display. Therefore, in the above quality control support method, the first control chart and the second control chart are displayed in the display period according to the difference between the measurement frequency of the quality control substance and the measurement frequency of the subject sample. Accordingly, the cause can be easily identified when there is an abnormality in the measurement result.

Second Embodiment

The second embodiment differs from the first embodiment in that the target value and the limit value of the LJ chart are determined by external quality control, and the target value and the limit value determined for each lot of the QC sample are used. In the following, the points different from the first embodiment will be particularly described with respect to the second embodiment.

FIG. 20 is a diagram showing an example of an LJ chart according to the second embodiment. As shown in FIG. 20, the "target value" (for example, "30") in the LJ chart is a reference value determined by aggregating the QC measurement results of each facility. "Upper limit value 3" (for example, "40") and "lower limit value 3" (for example, "20") are upper limit values and lower limit values determined by aggregating the QC measurement results of each facility. The "upper limit value 4" (for example, "37") and the "lower limit value 4" (for example, "23") are values set according to the respective values of the "upper limit value 3" and the "lower limit value 3". Each upper limit value and each lower limit value can be set by the user.

Figure 21:
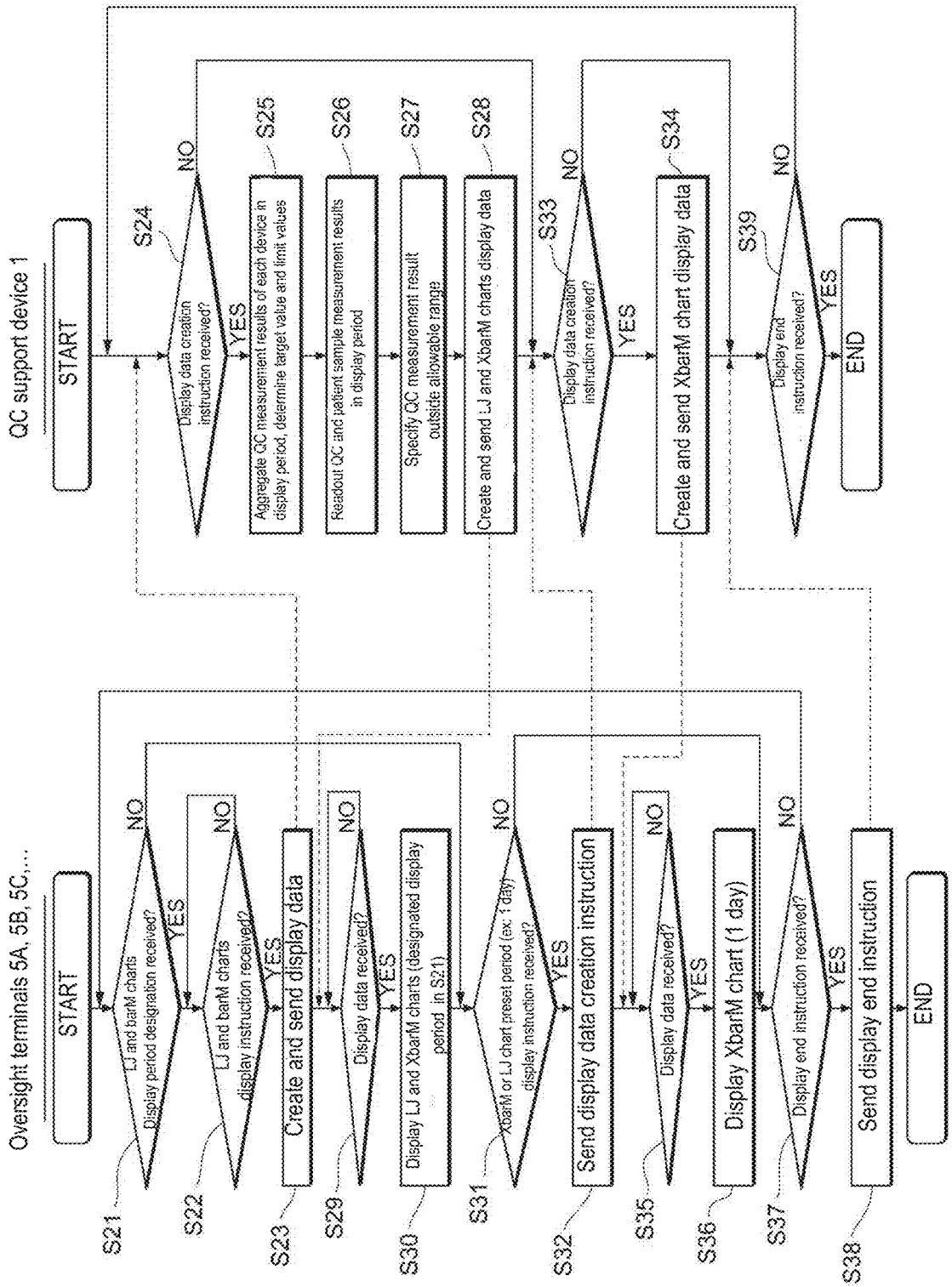
FIG. 21 is a flowchart showing an example of QC chart display processing according to the second embodiment.

FIG. 21 is a flowchart showing an example of the display process of the QC chart according to the second embodiment. The process steps S21 to S39 of FIG. 21, excluding step S25, correspond to the process steps S1 to S18 shown in FIG. 4. In step S25 shown in FIG. 21, the quality control support device 1 aggregates the QC measurement results of each facility during the display period, and determines the target value and each limit value shown in FIG. 20.

According to the second embodiment described above, in addition to the above effects in the first embodiment, the quality control support system 100 can be managed by the same management entity that manages each facility within a management group having a plurality of facilities such that external quality control becomes possible.

Third Embodiment

The third embodiment is different from the first embodiment in that the functions of the quality control support device 1 and the oversight terminal 5 in the first embodiment 1 are integrated in the quality control support device 1. In the following, the differences between the third embodiment and the first embodiment will be particularly described.

Figure 22:
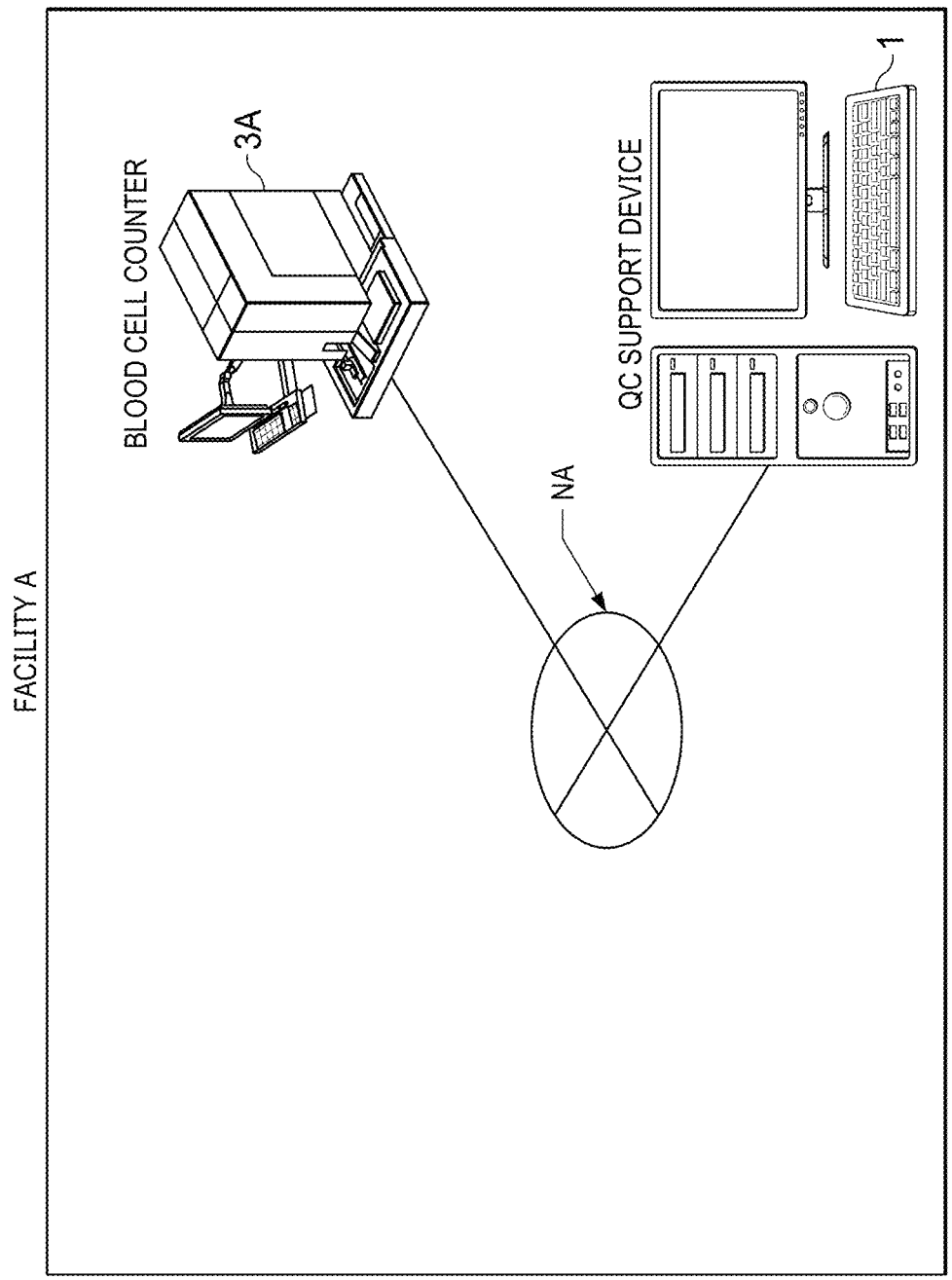
FIG. 22 is a diagram showing an example of a structure of a quality control support system according to a third embodiment.

As shown in FIG. 22, the quality control support device 1 is connected to the blood cell counter 3A via the network NA. The hardware configuration of the quality control support device 1 is the same as the configuration shown in FIG. 2.

Figure 23:
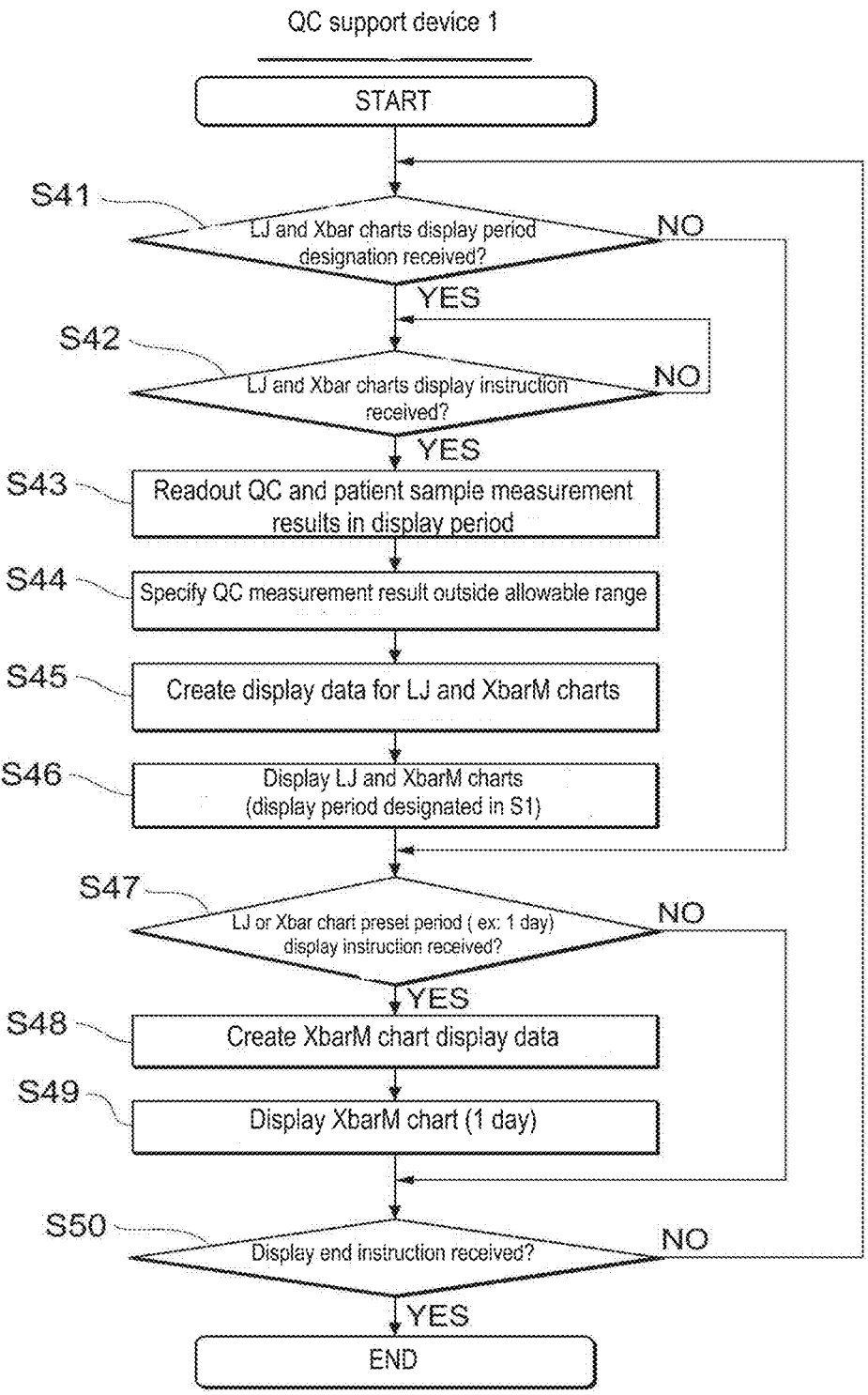
FIG. 23 is a flowchart showing an example of a QC chart display process according to a third embodiment.

FIG. 23 is a flowchart showing an example of the display process of the QC chart according to the third embodiment.
(Step S41)
The quality control support device 1 determines whether the person in charge has received the designation regarding the display period of the QC chart (for example, the LJ chart and the XbarM chart) to be displayed on the quality control support device 1. If the designation is received (YES in step S41), the process proceeds to step S42, whereas if the designation is not received (NO in step S41), the process proceeds to step S47.
(Step S42)
The quality control support device 1 determines whether a display instruction for the LJ chart and the XbarM chart has been received from the person in charge. If the designation is received (YES in step S42), the process proceeds to step S43, whereas if the designation is not received (NO in step S42), the process waits until the designation is received.
(Step S43)
The quality control support device 1 reads out the measurement data of the blood cell counter 3 stored in advance from the storage device 13 shown in FIG. 2.
(Step S44)
The quality control support device 1 identifies a QC measurement result outside the permissible range.
(Step S45)
The quality control support device 1 generates display data for displaying the LJ chart and the XbarM chart on the display included in the quality control support device 1.
(Step S46)
Based on the generated display data, the quality control support device 1 displays the LJ chart and the XbarM chart on the display for the display period (the period corresponding from Dec. 27, 2019 to Jan. 5, 2020) specified in step S41.
(Step S47)
The quality control support device 1 determines whether a display instruction for a predetermined period (for example, one day) (second period) on the XbarM chart or the LJ chart has been received from the person in charge via the pointing device. If the instruction is received (YES in step S47), the process proceeds to step S48, whereas if the instruction is not received (NO in step S47), the process proceeds to step S50.
(Step S48)
The quality control support device 1 generates display data for displaying the XbarM chart (second control chart) in the above day corresponding to the received instruction.
(Step S49)
The quality control support device 1 displays an XbarM chart (second control chart) based on the generated display data.
(Step S50)
The quality control support device 1 determines whether a display end instruction has been received from the person in charge. When the instruction is received (YES in step S50), the process ends, whereas when the instruction is not received (NO in step S50), the process returns to step S41. According to the third embodiment described above, it is not necessary to prepare the oversight terminal separately from the quality control support device 1.

Other Embodiments

Each of the above embodiments is for facilitating the understanding of the present invention, and does not limit the interpretation of the present invention. The present invention can be modified/improved (for example, combining each embodiment, omitting a part of the configuration of each embodiment) without departing from the spirit thereof, and the present invention also includes an equivalent thereof.

In each of the above embodiments, the blood cell counter 3 has been described as an example of the analyzer, but the present invention is not limited to a blood cell counter. As the analyzer, for example, another analyzer such as a blood coagulation measuring device, a biochemical analyzer, an immunoanalyzing device, a urine analyzer, or a nucleic acid analyzer may be adopted.

Figure 24:
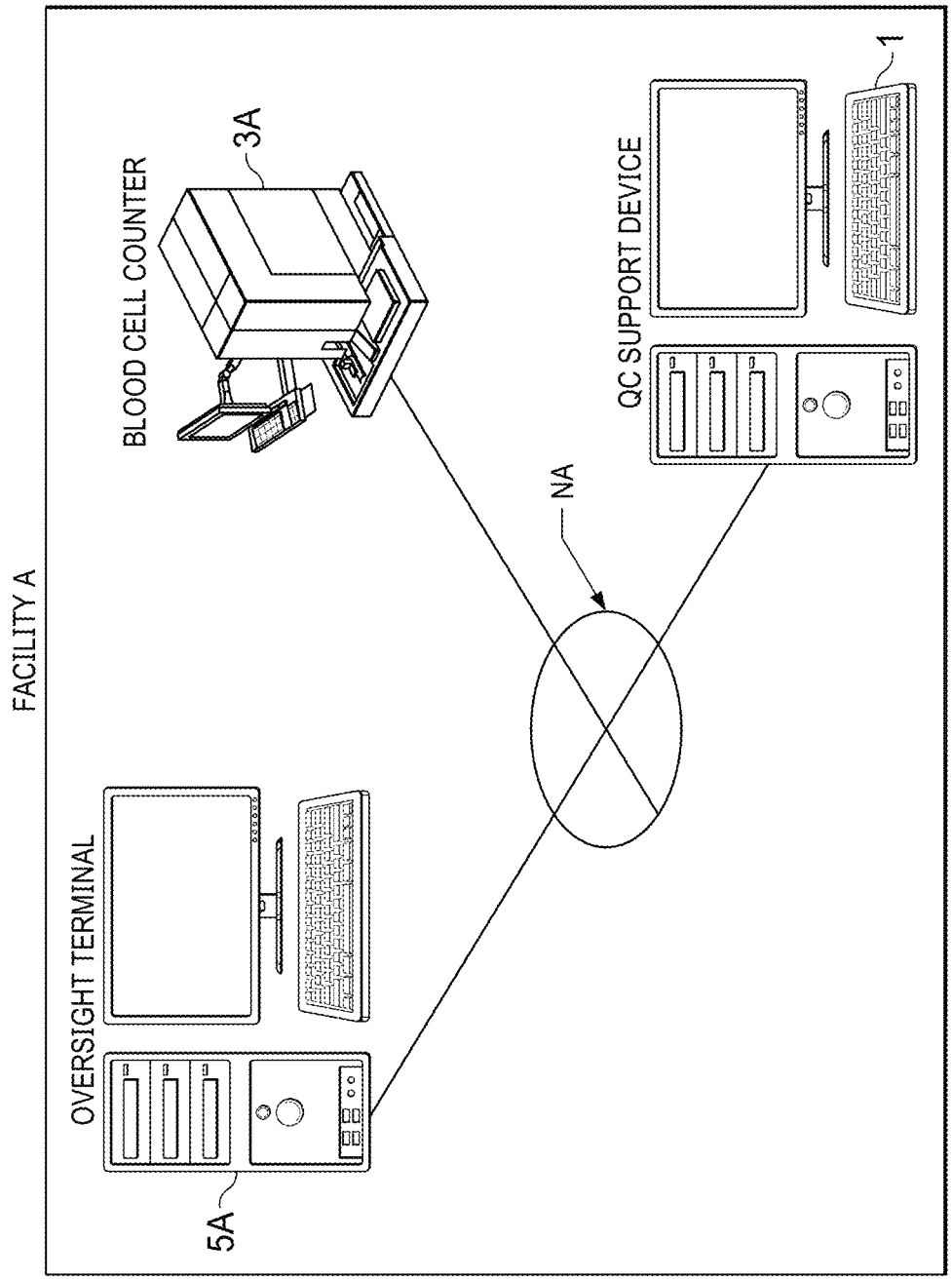
FIG. 24 is a diagram showing another example of the structure of the quality control support system according to the embodiment.

FIG. 24 is a diagram showing another example of the configuration of the quality control support system according to the embodiment. Although the quality control support device 1 is arranged in a support center different from the facility where the oversight terminal is arranged in FIG. 1, the quality control support device 1 also may be installed within the facility in which the oversight terminal 5 is installed as shown in FIG. 24.

What is claimed is:

1. A quality control support method for displaying a control chart of quality control related to an analyzer that measures a subject sample, the method comprising:
   measuring, by the analyzer capable of transmitting data, quality control substances;
   sending, from the analyzer to a quality control support device, results of the measured quality control substances by the analyzer;
   measuring, by the analyzer, subject samples;
   sending, from the analyzer to the quality control support device, results of the measured subject samples by the analyzer;
   generating, by the quality control support device, a first control chart showing the results of the measured quality control substances by the analyzer in a first period;
   receiving, by the quality control support device, a designation of a second period different from the first period, the second period being shorter than the first period and at least partially overlapping with the first period;
   generating, by the quality control support device, a second control chart showing results of the measured subject samples by the analyzer in the second period;
   displaying, by the quality control support device, the generated first control chart; and
   displaying, by the quality control support device, the generated second control chart.

2. The quality control support method according to claim 1, further comprising:
   receiving, by the quality control support device, the designation of the first period;
   wherein in the generating the first control chart, the first control chart is generated in the first period corresponding to the received designation of the first period.

3. The quality control support method according to claim 1, wherein
   the receiving the designation of the second period is executed after the first control chart is displayed.

4. The quality control support method according to claim 1, wherein
   the designation of the second period is received while the first control chart is displayed.

5. The quality control support method according to claim 1, further comprising:
   generating, by the quality control support device, a third control chart showing results of measured subject samples by the analyzer in a third period that is longer than the second period; and
   displaying, by the quality control support device, the generated third control chart;
   wherein in the receiving the designation of the second period, the designation of the second period is received by designating a partial area of the displayed third control chart, the second period corresponding to the designated partial area.

6. The quality control support method according to claim 5, wherein
   in the displaying the first control chart, a partial area of the first control chart is displayed in a manner different from that of other areas in the first control chart; and
   in the displaying the third control chart, a period corresponding to the partial area on the first control chart is displayed in a mode different from other periods in the third control chart.

7. The quality control support method according to claim 6, further comprising:
   changing, by the quality control support device, the partial area of the first control chart; and
   changing, by the quality control support device, display mode of the third control chart in accordance with the change of the partial area of the first control chart.

8. The quality control support method according to claim 5, further comprising:
   receiving, by the quality control support device, a change of the designated partial area of the third control chart.

9. The quality control support according to claim 5, further comprising:
   displaying, by the quality control support device, a relationship screen showing relationship between the second period and the third period.

10. The quality control support method according to claim 9, further comprising:
    receiving, by the quality control support device, a change of display period of the second control chart through the relationship screen; and
    displaying, by the quality control support device, the second control chart according to the received change.

11. The quality control support method according to claim 1, wherein
    in the receiving the designation of the second period, the designation of the second period is received by designating a partial area of the first control chart, the second period corresponding to the received partial area of the first control chart.

12. The quality control support method according to claim 1, wherein
    in the receiving the designation of the second period, a dialog for designating the second period is displayed, and the designation of the second period is received through the dialog.

13. The quality control support method according to claim 1, wherein
    when a predetermined event occurs within the first period, a mark indicating the occurrence of the event is displayed in the display of the first control chart.

14. The quality control support method according to claim 13, wherein
    the predetermined event includes at least one of error occurrence in the analyzer, calibration of the analyzer, or reagent exchange for the analyzer.

15. The quality control support method according to claim 13, wherein
    when the mark is selected, history related to the predetermined event is displayed.

16. The quality control support method according to claim 1, wherein
    the first control chart and the second control chart are displayed side by side.

17. The quality control support method according to claim 1, wherein
    the display of the first control chart is terminated when the second control chart is displayed.

18. A quality control support system for displaying a control chart of quality control related to an analyzer that measures a subject sample, the system comprising:
- a quality control support device comprising a first control unit;
- a terminal device, which is connected to the quality control support device via a network, comprising a second control unit and a display;
- wherein the first control unit of the quality control support device is configured to execute operations comprising:
- generating a first control chart showing results of measured quality control substances by the analyzer in a first period;
- receiving a designation of a second period different from the first period, the second period being shorter than the first period and at least partially overlapping with the first period;
- generating a second control chart showing results of measured subject samples by the analyzer in the second period; and
- the second control unit of the terminal device is configured to execute:
- displaying the generated first control chart on the display; and
- displaying the generated second control chart on the display.

19. A quality control support device for displaying a control chart of quality control related to an analyzer that measures a subject sample, the device comprising:
- a control unit; and
- a display;
- wherein the control unit is configured to execute operations comprising:
- generating a first control chart showing results of measured quality control substances by the analyzer in a first period;
- receiving a designation of a second period different from the first period, the second period being shorter than the first period and at least partially overlapping with the first period;
- generating a second control chart showing results of the measured subject samples by the analyzer in the second period;
- displaying the generated first control chart on the display; and
- displaying the generated second control chart on the display.

20. A quality control support device that is connected to a terminal device comprising a display via a network and displays a control chart of quality control related to an analyzer that measures a subject sample on a display of the terminal device, the quality control support devise comprising:
- a control unit,
- wherein the control unit is configured to execute operations comprising:
- generating a first control chart showing results of measured quality control substances by the analyzer in a first period;
- receiving a designation of a second period different from the first period, the second period being shorter than the first period and at least partially overlapping with the first period;
- generating a second control chart showing results of the measured subject samples by the analyzer in the second period;
- sending the generated first control chart to the terminal device; and
- sending the generated second control chart to the terminal device.

21. A non-transitory computer readable medium comprising a program in a quality control support device that displays a control chart of quality control related to an analyzer that is capable of transmitting data and measures a subject sample on a display of a terminal device, wherein the analyzer measures quality control substances, sends to the quality control support device results of the measured quality control substances, measures subject samples, and sends to the quality control support device results of the measured subject samples, the quality control support device and the terminal device being connected via a network, wherein, when the program is executed by the quality control support device, the program is configured to cause the quality control support device to perform:
- generating a first control chart showing the results of the measured quality control substances by the analyzer in a first period;
- receiving a designation of a second period different from the first period, the second period being shorter than the first period and at least partially overlapping with the first period;
- generating a second control chart showing results of the measured subject samples by the analyzer in the second period;
- sending the generated first control chart to the terminal device; and
- sending the generated second control chart to the terminal device.

22. A non-transitory computer readable medium comprising a program in a quality control support device comprising a display that displays a control chart of quality control related to an analyzer capable of transmitting data that measures a subject sample, wherein the analyzer measures quality control substances, sends to the quality control support device results of the measured quality control substances, measures subject samples, and sends to the quality control support device results of the measured subject samples, wherein, when the quality control support device executes the program, the program is configured to cause the quality control support device to perform:
- generating a first control chart showing the results of the measured quality control substances by the analyzer in a first period;
- receiving a designation of a second period different from the first period, the second period being shorter than the first period and at least partially overlapping with the first period;
- generating a second control chart showing results of the measured subject samples by the analyzer in the second period;
- displaying the generated first control chart on the display; and
- displaying the generated second control chart on the display.

23. A quality control support method for displaying a control chart of quality control related to an analyzer that measures a subject sample, the method comprising:
- measuring, by the analyzer capable of transmitting data, quality control substances;
- sending, from the analyzer to a quality control support device, results of the measured quality control substances by the analyzer;
- measuring, by the analyzer, subject samples;

sending, from the analyzer to the quality control support device, results of the measured subject samples by the analyzer;
generating, by the quality control support device, a first control chart showing the results of the measured quality control substances by the analyzer in a first period;
receiving, by the quality control support device, a designation of a second period different from the first period, the second period being shorter than the first period and at least partially overlapping with the first period;
generating, by the quality control support device, a second control chart showing results of the measured subject samples by the analyzer in the second period;
sending, by the quality control support device, the generated first control chart to a terminal device connected to the quality control support device via a network; and
sending, by the quality control support device, the generated second control chart to the terminal device.

* * * * *